United States Patent
Kawano

(10) Patent No.: US 10,578,546 B2
(45) Date of Patent: Mar. 3, 2020

(54) OPTICAL UNIT FOR MULTI-ANGLE OPTICAL CHARACTERISTIC MEASURING DEVICE, AND MULTI-ANGLE OPTICAL CHARACTERISTIC MEASURING DEVICE

(71) Applicant: KONICA MINOLTA, INC., Chiyoda-ku (JP)

(72) Inventor: Toshio Kawano, Sakai (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/326,102

(22) PCT Filed: Aug. 15, 2017

(86) PCT No.: PCT/JP2017/029391
§ 371 (c)(1),
(2) Date: Feb. 15, 2019

(87) PCT Pub. No.: WO2018/037973
PCT Pub. Date: Mar. 1, 2018

(65) Prior Publication Data
US 2019/0195783 A1    Jun. 27, 2019

(30) Foreign Application Priority Data
Aug. 26, 2016    (JP) ................. 2016-165570

(51) Int. Cl.
*G01J 3/00*    (2006.01)
*G01N 21/25*    (2006.01)
(Continued)

(52) U.S. Cl.
CPC .............. *G01N 21/255* (2013.01); *G01J 3/51* (2013.01); *G01N 21/27* (2013.01); *G01N 21/47* (2013.01);
(Continued)

(58) Field of Classification Search
CPC ................. G01N 21/255; G01N 21/27; G01N 2201/0636; G01N 21/64; G01J 1/58; G01J 3/02; G06K 9/00
See application file for complete search history.

(56) References Cited

U.S. PATENT DOCUMENTS

| 2011/0096967 | A1* | 4/2011 | Oda ................... G01N 21/6456 |
| | | | 382/128 |
| 2015/0253190 | A1* | 9/2015 | Seo ........................... G01J 3/02 |
| | | | 356/328 |

FOREIGN PATENT DOCUMENTS

| JP | 6-201471 | 7/1994 |
| JP | 2004-020263 | 1/2004 |

(Continued)

OTHER PUBLICATIONS

Written Opinion dated issued in corresponding Application No. PCT/JP2017/029391.
(Continued)

*Primary Examiner* — Abdullahi Nur
(74) *Attorney, Agent, or Firm* — Cozen O'Connor

(57) ABSTRACT

A multi-angle optical characteristic measuring device and an optical unit therefor include: an illuminating portion that irradiates a measurement point with an illuminating light beam; a plurality of reflecting mirrors that are arranged facing the measurement point at a plurality of different observation angles, and modify traveling directions of measurement light beams emitted from the measurement point in response to the illuminating light beam; one light receiving optical system that receives the measurement light beams from the plurality of reflecting mirrors; and a two-dimensional detecting portion that detects the measurement light beams received by the light receiving optical system, and the plurality of reflecting mirrors modifies the traveling directions of the measurement light beams such that the two-
(Continued)

dimensional detecting portion detects the measurement light beams at different positions on the two-dimensional detecting portion.

20 Claims, 9 Drawing Sheets

(51) Int. Cl.
    *G01J 3/51*     (2006.01)
    *G01N 21/47*     (2006.01)
    *G01N 21/27*     (2006.01)

(52) U.S. Cl.
    CPC ... *G01N 21/474* (2013.01); *G01N 2021/4711* (2013.01); *G01N 2201/0636* (2013.01)

(56) References Cited

FOREIGN PATENT DOCUMENTS

| | | |
|---|---|---|
| JP | 2005-009987 | 1/2005 |
| JP | 2006-10508 | 1/2006 |
| JP | 2012-2762 | 1/2012 |
| JP | 2012-233764 | 11/2012 |
| WO | WO 2016/093079 | 6/2019 |

OTHER PUBLICATIONS

International Search Report issued in corresponding Application No. PCT/JP2017/029391.

* cited by examiner

A.

B.

OPTICAL UNIT FOR MULTI-ANGLE OPTICAL CHARACTERISTIC MEASURING DEVICE, AND MULTI-ANGLE OPTICAL CHARACTERISTIC MEASURING DEVICE

RELATED APPLICATIONS

This is a U.S. National Phase Application under 35 USC 371 of International Application PCT/JP2017/029391 filed on Aug. 15, 2017.

This application claims the priority of Japanese application no. 2016-165570 filed Aug. 26, 2016, the entire content of which is hereby incorporated by reference.

TECHNICAL FIELD

The present invention relates to an optical unit for a multi-angle optical characteristic measuring device used in a multi-angle optical characteristic measuring device for measuring predetermined optical characteristics of a measurement target or subject with multi-angle geometry and to the multi-angle optical characteristic measuring device.

BACKGROUND ART

Metallic painting and pearl color painting used for automotive painting and the like contain flake-like aluminum pieces and mica pieces called glitter materials in paint films, and exhibit what is called a metallic effect and a pearl effect. These effects are attributable to the fact that the contribution of glitter materials to the reflection characteristics varies depending on the illumination direction and the observation direction. Devices for evaluating such metallic painting and pearl color painting have been known conventionally.

A coating film containing such a glitter material is evaluated by calculating color information of a subject (for example, tristimulus values) as the predetermined optical characteristics based on the spectroscopic result obtained with multi-angle geometry. Such an evaluation is performed, for example, using a multi-angle colorimeter disclosed in Patent Literature 1. The multi-angle geometry includes geometry of multidirectional illumination/unidirectional light reception in which light beams are radiated to a measurement surface of a subject from a plurality of different directions and received in a single direction, and geometry of unidirectional illumination/multidirectional light reception in which light beams are radiated to a measurement surface of a subject from a single direction and received in a plurality of different directions. The geometry is defined in, for example, DIN-6175-2 of DIN standards (German industrial standards) and the like.

Further, a coating film containing a glitter material is evaluated by calculating brilliance as the predetermined optical characteristics based on an image of a subject obtained with multi-angle geometry. Such an evaluation is performed, for example, using a brilliance evaluation device disclosed in Patent Literature 2. The brilliance is quantified from the image of the subject using the number of bright points due to glitter material reflection or the distribution of the size of the bright points.

In order to radiate light (or receive (observe) light) from a plurality of directions with the multi-angle geometry, an optical system and a light source (or a light receiving portion) are required for each angle, which makes the configuration complicated. Furthermore, since it is necessary to change the illumination direction (or the light receiving direction (observation direction)), the measurement time is long. For this reason, for example, a multi-angle colorimeter of Patent Literature 3 has been proposed. The multi-angle colorimeter disclosed in Patent Literature 3 includes: an annular first reflecting mirror (for example, a toroidal mirror) having a center axis on a sample surface; a second reflecting mirror (for example, a conical mirror) provided near a focal circumference including a group of focal points of the first reflecting mirror; a relay optical system for forming an image of the focal circumference around the central axis as an optical axis; an aperture plate provided on an image forming surface of the relay optical system and having one or more sample light apertures on an aperture circumference that coincides with the image of the focal circumference; and a light receiving sensor provided behind the sample light aperture to receive reflected light reflected by the sample. Parallel light fluxes emitted from the sample surface toward the first reflecting mirror are reflected by the first reflecting mirror, converged on the focal circumference, reflected by the second reflecting mirror provided near the focal circumference to enter the relay optical system, and converged on the aperture circumference to pass through the sample light aperture and enter the light receiving sensor.

The multi-angle colorimeter disclosed in Patent Literature 3 is advantageous because the optical system is simplified by the above configuration. However, it is necessary to make an adjustment so that the focal plane of the first reflecting mirror (toroidal mirror) coincides with the focal plane of the relay optical system. In this adjustment, since light beams from the respective light receiving directions (observation directions) are reflected by the single first reflecting mirror, the traveling directions of the light beams from the respective light receiving directions (observation directions) must be adjusted at the same time by adjusting the position and posture of the single first reflecting mirror. Further, since the position and posture of the second reflecting mirror (conical mirror) also relate to the adjustment, it is difficult to assemble and adjust these components. Generally, the toroidal mirror and the conical mirror are expensive due to their high cost of production.

CITATION LIST

Patent Literature

Patent Literature 1: JP 2012-233764 A
Patent Literature 2: JP 2004-020263 A
Patent Literature 3: JP 2005-009987 A

SUMMARY OF INVENTION

The present invention has been made in view of the above circumstances, and an object thereof is to provide an optical unit for a multi-angle optical characteristic measuring device and a multi-angle optical characteristic measuring device capable of facilitating assembly and adjustment of multi-angle geometry and reducing cost.

In order to realize (at least one of) the above objects, an optical unit for a multi-angle optical characteristic measuring device and a multi-angle optical characteristic measuring device reflecting one aspect of the present invention include: an illuminating portion that irradiates a measurement point with an illuminating light beam; a plurality of reflecting mirrors that are arranged facing the measurement point at a plurality of different observation angles, and modify traveling directions of measurement light beams emitted from the measurement point in response to the illuminating light beam; one light receiving optical system that receives the measurement light beams from the plurality of reflecting mirrors; and a two-dimensional detecting portion that detects the measurement light beams received by the light receiving optical system, and the plurality of reflecting mirrors modifies the traveling directions of the measurement light beams such that the two-dimensional detecting portion detects the measurement light beams at different positions on the two-dimensional detecting portion.

An optical unit for a multi-angle optical characteristic measuring device and a multi-angle optical characteristic measuring device according to the present invention can facilitate assembly and adjustment of multi-angle geometry and reduce cost.

Advantages and features provided by one or more embodiments of the invention are fully understood from the detailed description given below and the accompanying drawings. These detailed description and accompanying drawings are given by way of example only and do not define the limits of the invention.

DESCRIPTION OF EMBODIMENTS

One or more embodiments of the present invention will now be described with reference to the drawings. However, the scope of the invention is not limited to the disclosed embodiments. It is to be noted that identical components are denoted by the same reference signs in drawings, and the description thereof is omitted as appropriate. In the present specification, components are collectively denoted by reference signs without suffixes, and are distinguished from each other by being denoted by reference signs with suffixes.

Figure 1:
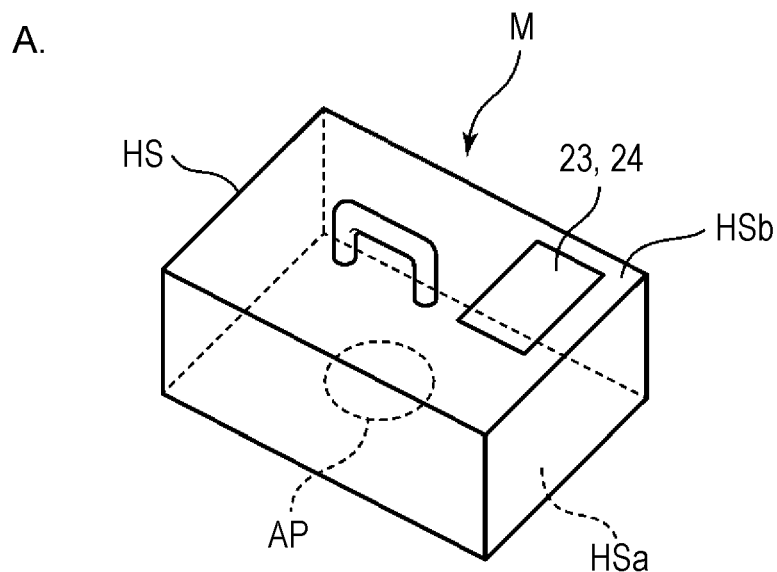
FIG. 1 is a schematic view illustrating the appearance of a multi-angle optical characteristic measuring device according to an embodiment.
Figure 1:
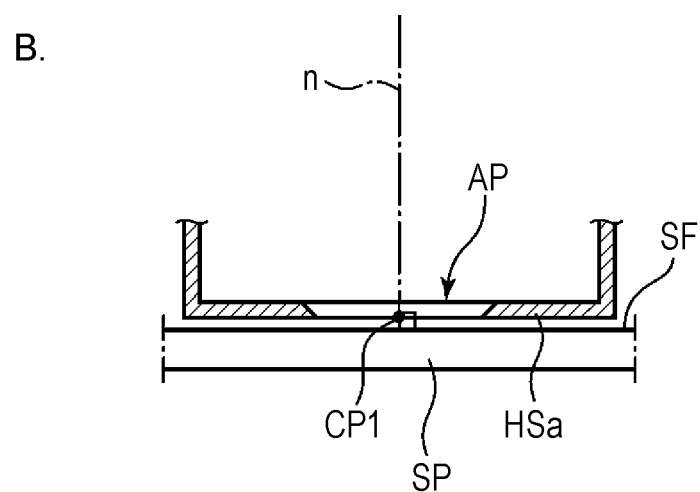
Figure 2:
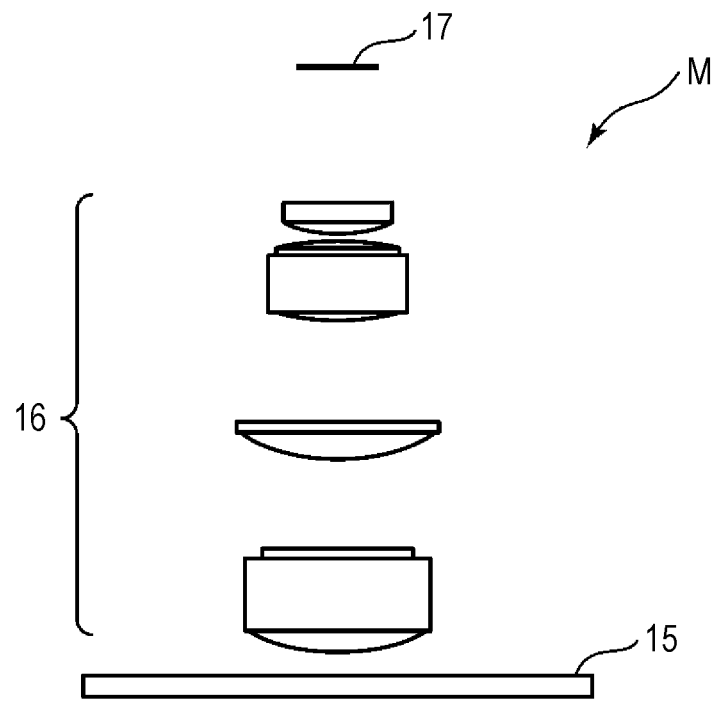
FIG. 2 is a front view mainly illustrating the configuration of an optical system in the multi-angle optical characteristic measuring device.
Figure 2:
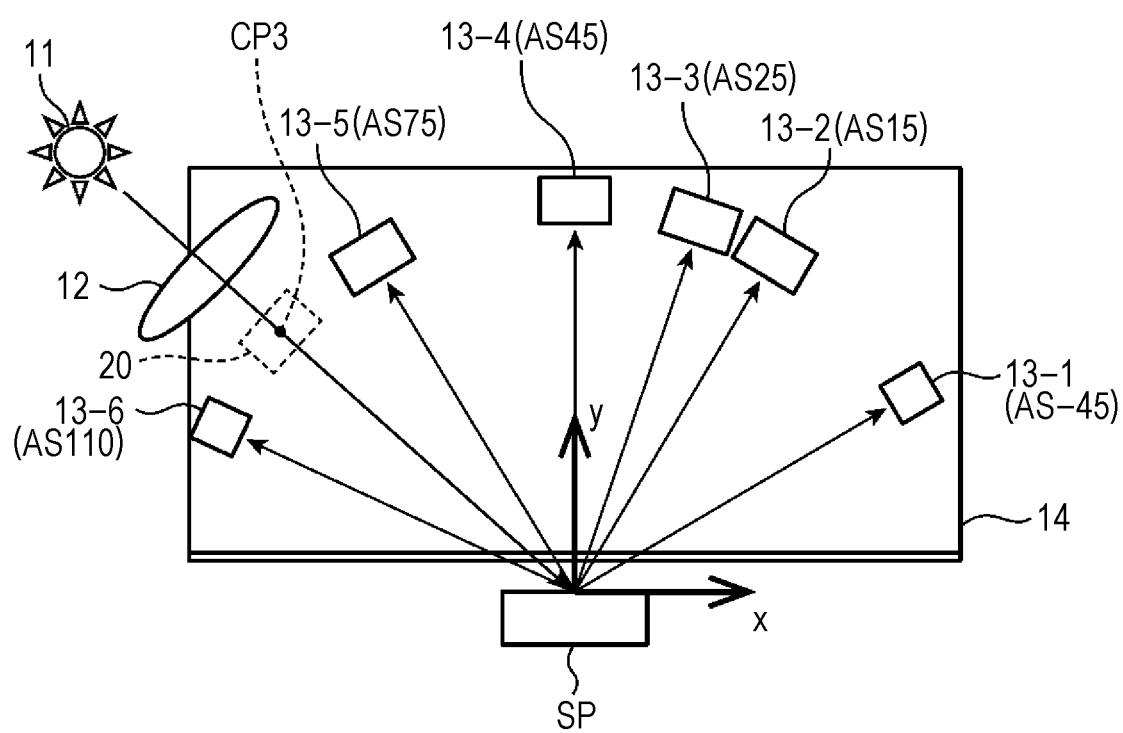
Figure 3:
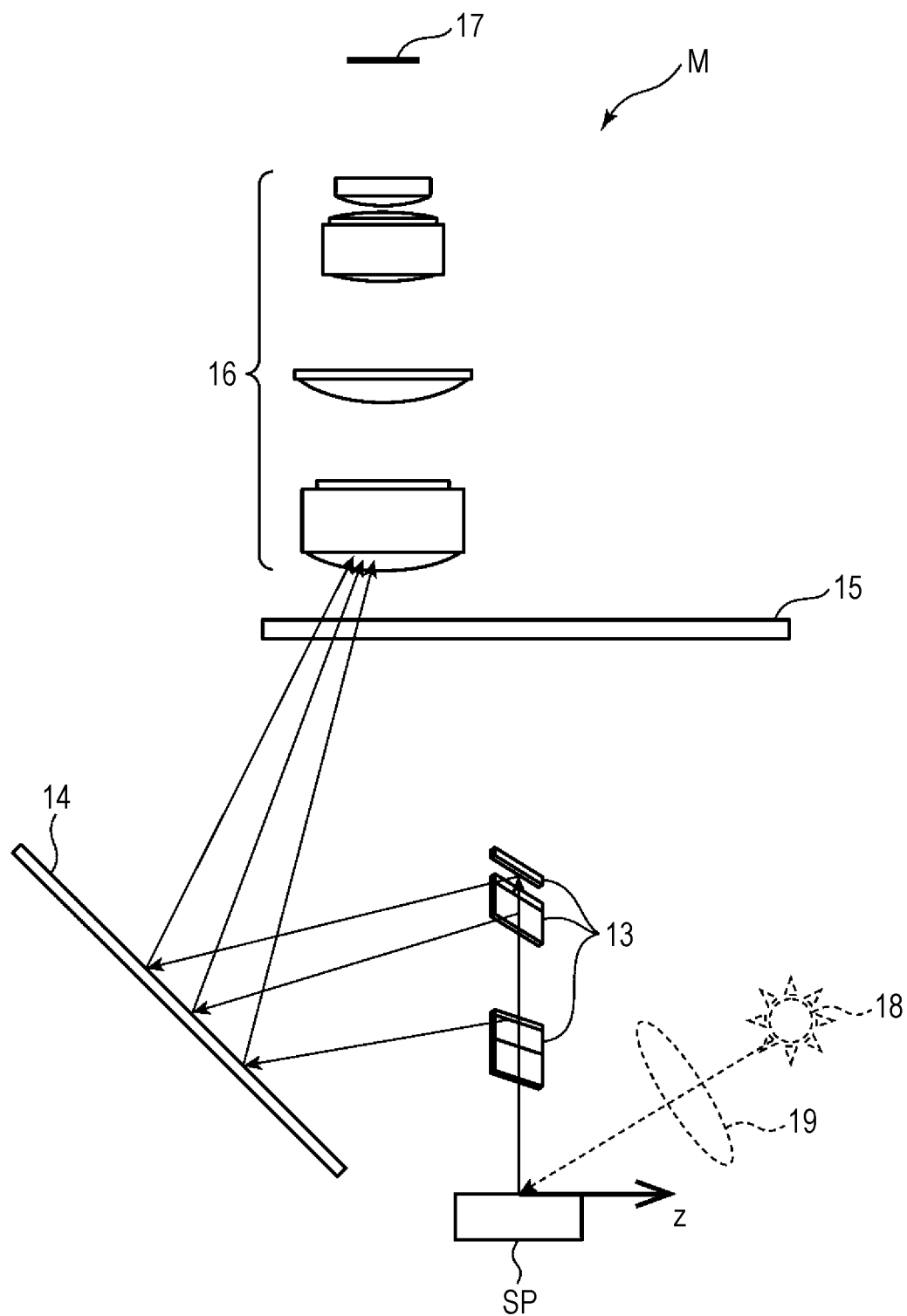
FIG. 3 is a side view mainly illustrating the configuration of the optical system in the multi-angle optical characteristic measuring device.
Figure 4:
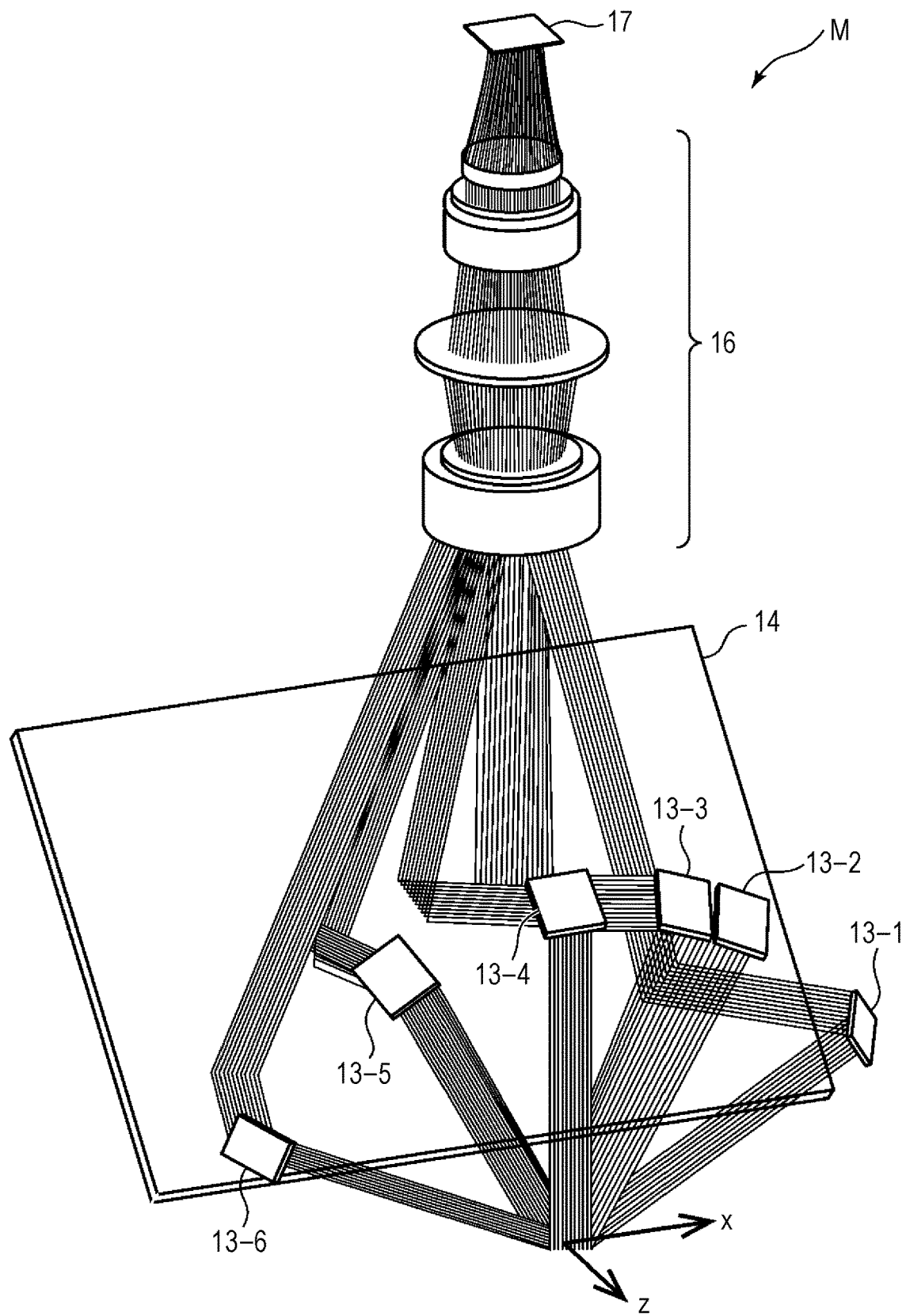
FIG. 4 is a perspective view mainly illustrating the optical path of the optical system in the multi-angle optical characteristic measuring device.
Figure 5:
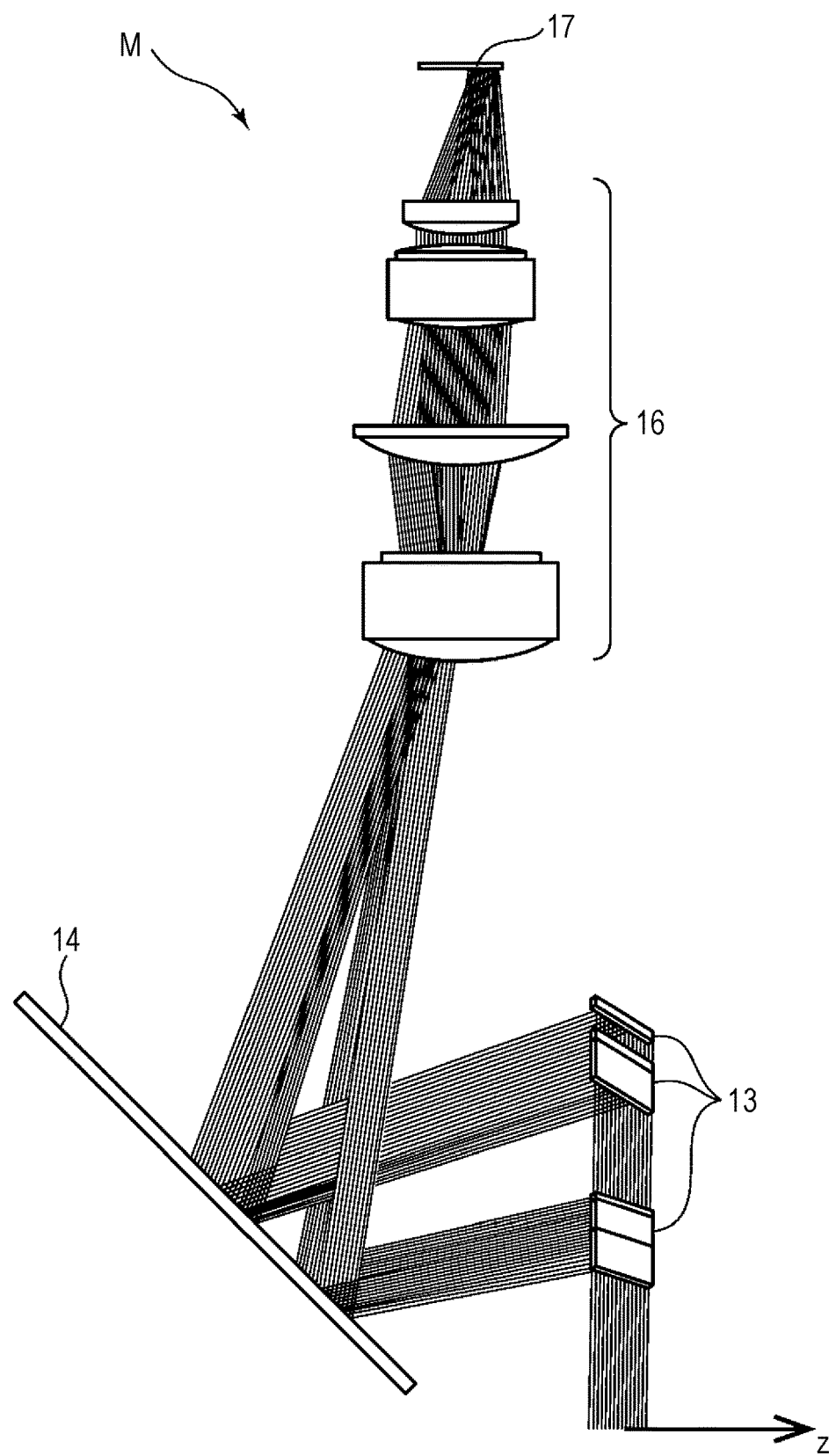
FIG. 5 is a side view mainly illustrating the optical path of the optical system in the multi-angle optical characteristic measuring device.
Figure 6:
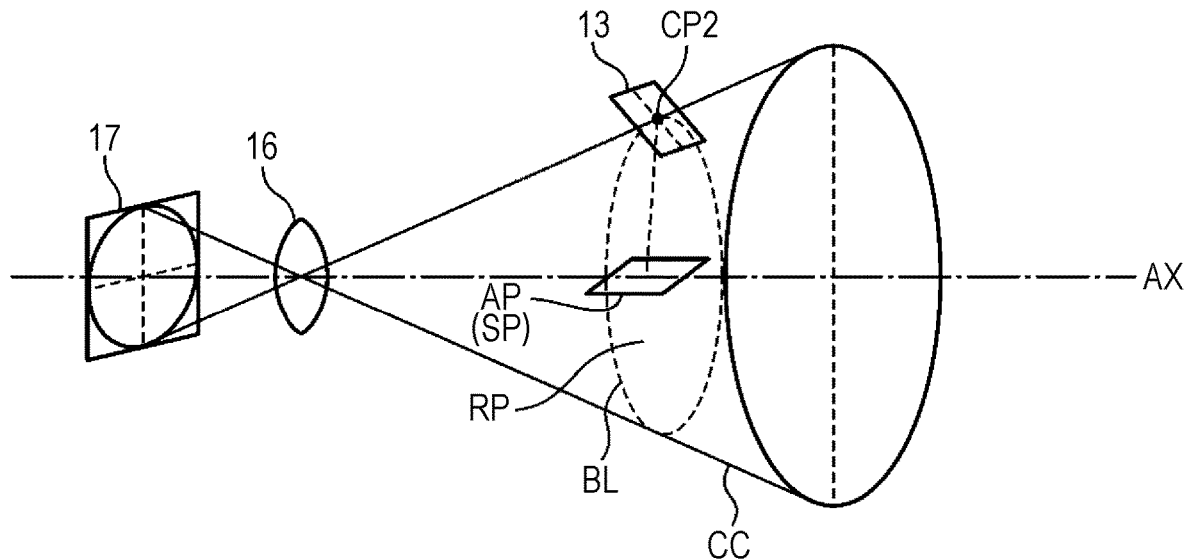
FIG. 6 is a view for explaining the arrangement position of a first reflecting mirror in the multi-angle optical characteristic measuring device.
Figure 7:
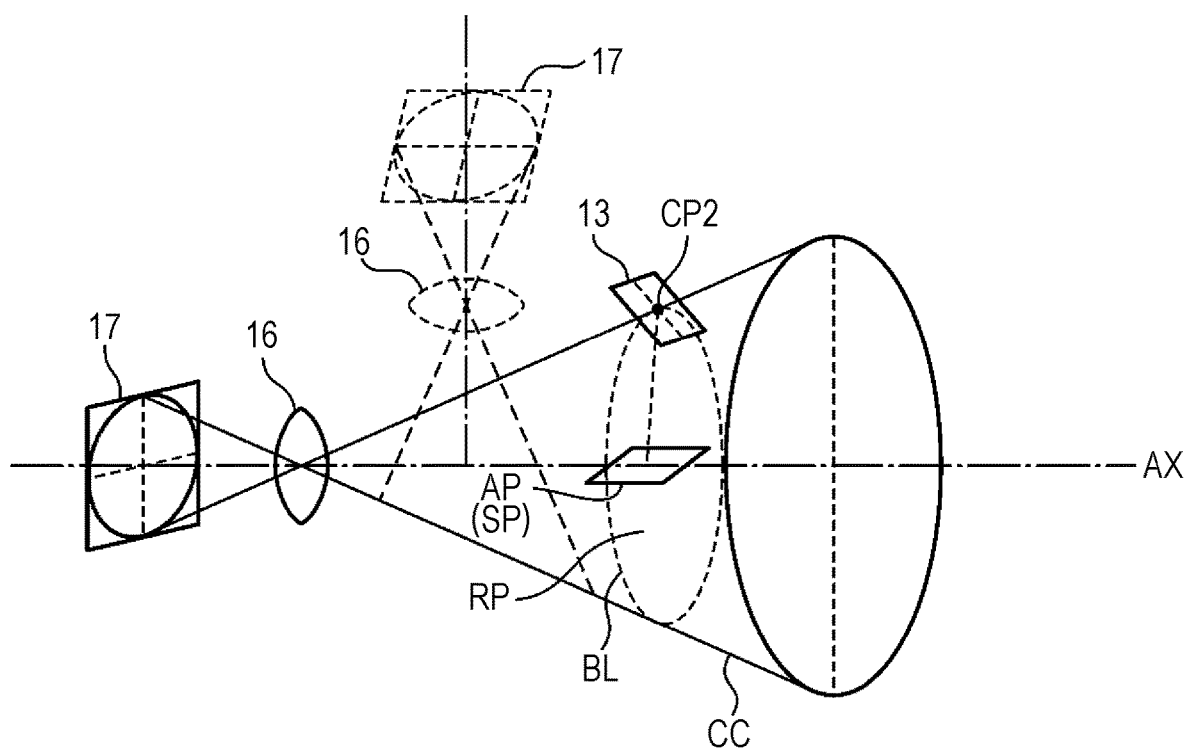
FIG. 7 is a view for explaining the role of a second reflecting mirror in the multi-angle optical characteristic measuring device.
Figure 8:
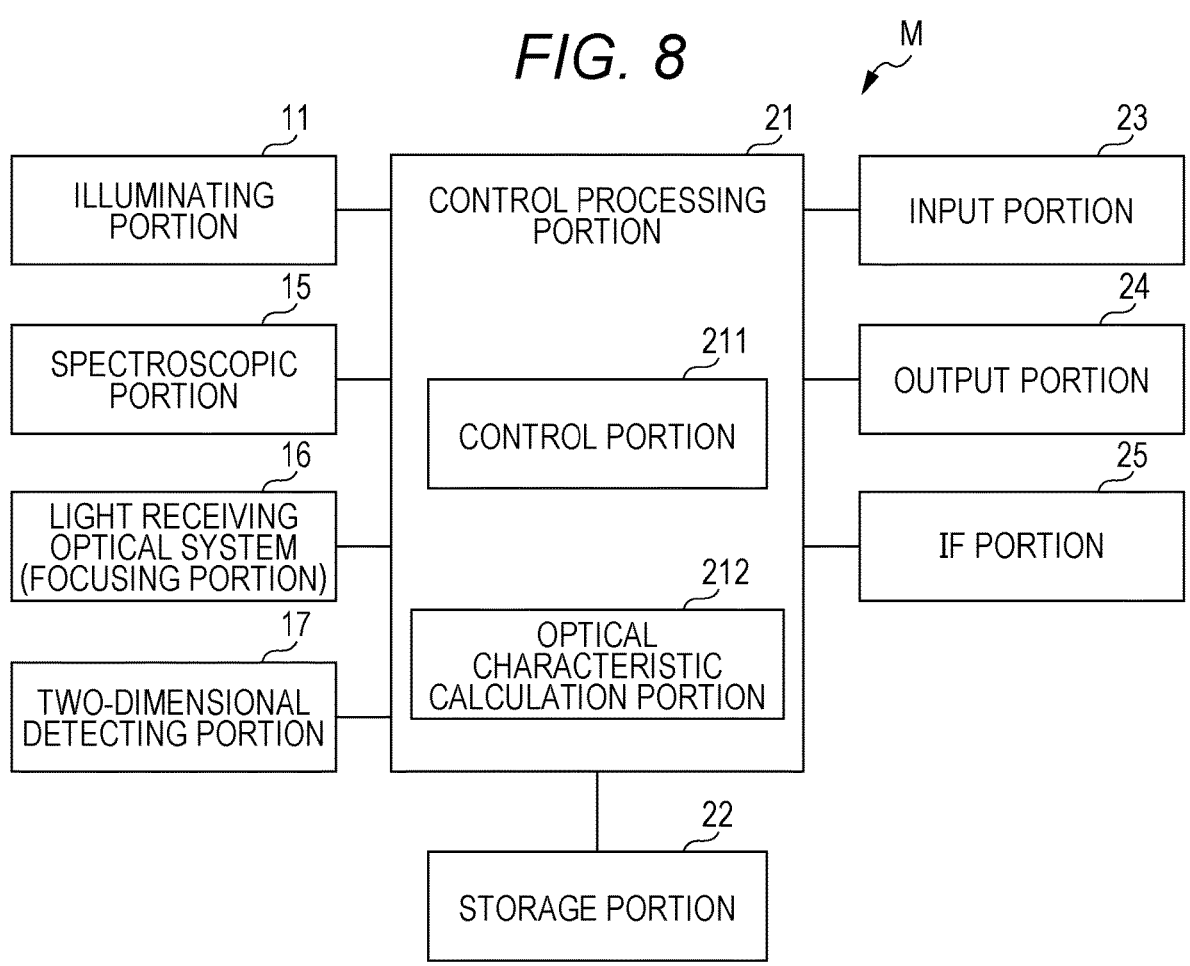
FIG. 8 is a diagram mainly illustrating the electrical configuration of the multi-angle optical characteristic measuring device.

FIG. 1 is a schematic view illustrating the appearance of a multi-angle optical characteristic measuring device according to an embodiment. FIG. 1A is a perspective view, and FIG. 1B is a cross-sectional view taken along a section line including a measurement aperture. FIG. 2 is a front view mainly illustrating the configuration of an optical system in the multi-angle optical characteristic measuring device according to the embodiment, and FIG. 3 is a side view thereof. FIG. 4 is a perspective view mainly illustrating the optical path of the optical system in the multi-angle optical characteristic measuring device according to the embodiment, and FIG. 5 is a side view thereof. FIG. 6 is a view for explaining the arrangement position of a first reflecting mirror in the multi-angle optical characteristic measuring device according to the embodiment. FIG. 7 is a view for explaining the role of a second reflecting mirror in the multi-angle optical characteristic measuring device according to the embodiment. FIG. 8 is a diagram mainly illustrating the electrical configuration of the multi-angle optical characteristic measuring device according to the embodiment.

Referring to FIGS. 1 to 8, the multi-angle optical characteristic measuring device M according to the embodiment includes an illuminating portion 11, an illumination optical system 12, a plurality of first reflecting mirrors 13 (13-1 to 13-6), a second reflecting mirror 14, a spectroscopic portion 15, a light receiving optical system 16, a two-dimensional detecting portion 17, a control processing portion 21, a storage portion 22, an input portion 23, an output portion 24, an interface portion (IF portion) 25, and a housing HS. The illuminating portion 11, the plurality of first reflecting mirrors 13 (13-1 to 13-6), the second reflecting mirror 14, the spectroscopic portion 15, the light receiving optical system 16, and the two-dimensional detecting portion 17 are an example of an optical unit for a multi-angle optical characteristic measuring device. The optical unit for a multi-angle optical characteristic measuring device according to the present embodiment further includes the illumination optical system 12.

The housing HS is a box-like member having, for example, a rectangular parallelepiped shape and containing the illuminating portion 11, the illumination optical system 12, the plurality of first reflecting mirrors 13, the second reflecting mirror 14, the spectroscopic portion 15, the light receiving optical system 16, the two-dimensional detecting portion 17, the control processing portion 21, the storage portion 22, the input portion 23, the output portion 24, and the IF portion 25. As illustrated in FIG. 1A, a through hole or measurement aperture AP is formed at an appropriate position in a bottom plate (floor plate) HSa of the housing HS. On a top plate (ceiling plate) HSb of the housing HS, the input portion 23 and the output portion 24 are arranged at an appropriate position as an operation display panel.

When the predetermined optical characteristics of a measurement target or subject SP are measured with the multi-angle optical characteristic measuring device M having the housing HS, as illustrated in FIG. 1B, the bottom plate HSa faces a measurement surface SF of the subject SP. In this case, preferably, the multi-angle optical characteristic measuring device M is arranged on the subject SP such that the normal n of the aperture plane passing through a central position CP1 of the measurement aperture AP coincides with the normal of the measurement surface SF.

The illuminating portion 11 is a device that is connected to the control processing portion 21 and irradiates a predetermined measurement point on the measurement surface with an illuminating light beam of a predetermined wavelength band under the control of the control processing portion 21. The predetermined measurement point may be appropriately set. In the present embodiment, for example, the predetermined measurement point is the central position CP1 of the measurement aperture AP. In this case, the measurement surface including the measurement point is the aperture plane of the measurement aperture AP. The predetermined wavelength band is appropriately set according to the predetermined optical characteristics to be measured. In the present embodiment, for example, the predetermined wavelength band is a wavelength band of visible light. The illuminating portion 11 includes, for example, a light source such as a xenon lamp or a white LED, and a drive circuit that is connected to the control processing portion 21 and drives the light source under the control of the control processing portion 21.

The illumination optical system 12 is an optical system that collimates (makes parallel) an illuminating light beam emitted from the illuminating portion 11 and guides it to the measurement point. The illumination optical system 12 includes, for example, one or more optical lenses or the like. The illumination optical system 12 is arranged so as to guide the illuminating light beam to the measurement point from the illumination direction (for example, direction of 45°) of multi-angle geometry adopted in the multi-angle optical characteristic measuring device M. That is, the illumination optical system 12 is arranged such that the optical axis of the illumination optical system 12 coincides with the illumination direction of the multi-angle geometry.

The plurality of first reflecting mirrors 13 are optical elements arranged facing the measurement point at a plurality of different observation angles (light receiving angles) APn. The plurality of first reflecting mirrors 13 modify the traveling directions of measurement light beams emitted from the measurement point in response to the illuminating light beam. In the present embodiment, the plurality of first reflecting mirrors 13 modify the traveling directions of measurement light beams from the measurement point such that the two-dimensional detecting portion 17 detects the measurement light beams at different positions on the detection surface (light receiving surface) of the two-dimensional detecting portion 17. In the present embodiment, each of the plurality of first reflecting mirrors 13 is arranged on a virtual reference plane (multi-angle geometric plane) RP (see FIG. 6) including the normal of the measurement surface passing through the measurement point and the optical axis of the illuminating portion 11. In the present embodiment, the plurality of first reflecting mirrors 13 are arranged at an equal distance from the measurement point, and modify the traveling directions of measurement light beams from the measurement point toward the entrance pupil of the light receiving optical system 16.

The plurality of observation angles (light receiving angles) APn are set according to the multi-angle geometry adopted in the multi-angle optical characteristic measuring device M. For example, in the present embodiment, the plurality of observation angles are −15° (AS−15), +15° (AS15), +25° (AS25), +45° (AS45), +75° (AS75), and +110° (AS110), where the specular reflection direction of an illuminating light beam is reference 0°, the direction toward (approaching) the illumination optical system 12 (counterclockwise direction in FIG. 2) is the positive direction, and the direction away from (separating from) the illumination optical system 12 (clockwise direction in FIG. 2) is the negative direction. Correspondingly, this plurality of first reflecting mirrors 13 includes the six 1a-th to 1f-th reflecting mirrors 13-1 to 13-6 in the present embodiment.

The 1a-th mirror 13-1 is arranged facing the measurement point at an observation angle of −15°. The 1b-th reflecting mirror 13-2 is arranged facing the measurement point at an observation angle of +15°. The 1c-th reflecting mirror 13-3 is arranged facing the measurement point at an observation angle of +25°. The 1d-th reflecting mirror 13-4 is arranged facing the measurement point at an observation angle +45°. The 1e-th reflection mirror 13-5 is arranged facing the measurement point at an observation angle +75°. The 1f-th reflecting mirror 13-6 is arranged facing the measurement point at an observation angle of +110°.

The arrangement of each of these six 1a-th to 1f-th reflecting mirrors 13-1 to 13-6 will be described in more detail with reference to FIG. 6. In FIG. 6, for easier understanding of the arrangement of each of the 1a-th to 1f-th reflecting mirrors 13-1 to 13-6, the illuminating portion 11, the illumination optical system 12, and the spectroscopic portion 15 are omitted, the second reflecting mirror 14 is removed (not provided), and the two-dimensional detecting portion 17 and the light receiving optical system 16 are each arranged at an arrangement position where an optical axis AX of the two-dimensional detecting portion 17 and the light receiving optical system 16 coincides with a virtual perpendicular line passing through the measurement point (in the present embodiment, the central position CP1 of the measurement aperture AP) and orthogonal to the reference plane RP. Therefore, the optical axis AX of the two-dimensional detecting portion 17 and the light receiving optical system 16 is included in the aperture plane (measurement surface) of the measurement aperture AP. In FIG. 6, one of the 1a-th to 1f-th reflecting mirrors 13-1 to 13-6 is representatively illustrated as the first reflecting mirror 13 (that is, the remaining first reflecting mirrors 13 are omitted from FIG. 6). In FIG. 6, the first reflecting mirror 13 is arranged in the direction of an observation angle (light receiving angle) ASn of the first reflecting mirror 13 such that the optical axis of the first reflecting mirror 13 coincides with the generatrix of a cone CC and that a second arrangement position CP2 of the first reflecting mirror 13 is located on an intersection line BL between the reference plane RP and the side surface of the cone CC. The apex of the cone CC is the center of the entrance pupil of the light receiving optical system 16, and the half apex angle of the cone CC is the angle formed by the principal ray of the observation angle (light receiving angle) ASn and the optical axis AX.

Preferably, each of the plurality of first reflecting mirrors 13 (13-1 to 13-6) does not have a focal point (converging point) of a measurement light beam between the measurement point and the incident surface of the light receiving optical system 16. Preferably, each of the plurality of first reflecting mirrors 13 (13-1 to 13-6) is a plane mirror having no optical power. The optical power is also called refracting power and is the reciprocal of the focal length in air having a refractive index of 1.

The second reflecting mirror 14 is an optical element that modifies the traveling directions of measurement light beams from the plurality of first reflecting mirrors 13 (13-1 to 13-6) toward the light receiving optical system 16. In the present embodiment, the light receiving optical system 16 is arranged above the measurement point. The second reflecting mirror 14 is, for example, a plane mirror, and is arranged so as to modify the traveling directions of measurement light beams from the plurality of reflecting mirrors 13 (13-1 to 13-6) toward the light receiving optical system 16 arranged in this position.

As described with reference to FIG. 6, the multi-angle optical characteristic measuring device M does not need to include the second reflecting mirror 14, but may include the illuminating portion 11, the illumination optical system 12, the plurality of first reflecting mirrors 13, the spectroscopic portion 15, the light receiving optical system 16, the two-dimensional detecting portion 17, the control processing portion 21, the storage portion 22, the input portion 23, the output portion 24, the IF portion 25, and the housing HS. However, in this case, as will be understood from FIG. 6, the housing HS is a member having an inverted L shape (that is, Γ shape) in a side view, instead of a rectangular parallelepiped shape as illustrated in FIG. 1A. As illustrated by the broken lines in FIG. 7, the second reflecting mirror 14 functions so as to rotate the part of the optical axis AX illustrated in FIG. 6 passing through the two-dimensional detecting portion 17 and the light receiving optical system 16 by 90° in the clockwise direction in FIG. 6, so that the two-dimensional detecting portion 17 and the light receiving optical system 16 can be arranged above the measurement point. In the present embodiment, the two-dimensional detecting portion 17 and the light receiving optical system 16 are arranged in parallel with the part of the optical axis AX passing through the two-dimensional detecting portion 17 and the light receiving optical system 16 and the normal n passing through the measurement point on a virtual orthogonal plane orthogonal to the reference plane RP (in the present embodiment, aperture plane (measurement surface) of the measurement aperture AP). By providing the second reflecting mirror 14 in this manner, the two-dimensional detecting portion 17 and the light receiving optical system 16 can be arranged above the measurement point, so that the housing HS having a rectangular parallelepiped shape can be used.

In the present embodiment, the part of the optical axis passing through the two-dimensional detecting portion 17 and the light receiving optical system 16 is rotated by 90° in the clockwise direction in FIG. 6. Alternatively, in a case where second reflecting mirror 14 is not provided, as long as the two-dimensional detecting portion 17 and the light receiving optical system 16 are each arranged at an arrangement position where the optical axis of the two-dimensional detecting portion 17 and the light receiving optical system 16 coincides with a virtual perpendicular line passing through the measurement point and orthogonal to the reference plane RP, the part of the optical axis passing through the two-dimensional detecting portion 17 and the light receiving optical system 16 may be rotated by any angle in the range of 0° to 90° in the clockwise direction in FIG. 6. In the present embodiment, the second reflecting mirror 14 includes one reflecting mirror. Alternatively, the number of second reflecting mirrors 14 may be equal to the number of the plurality of first reflecting mirrors 13.

The spectroscopic portion 15 is an optical element that is connected to the control processing portion 21 and spectrally separates and emit incident light under the control of the control processing portion 21. In the present embodiment, the spectroscopic portion 15 is arranged between the measurement point and the two-dimensional detecting portion 17, for example, in front of the light receiving optical system 16. The spectroscopic portion 15 spectrally separates a measurement light beam as the incident light, and emits it to the light receiving optical system 16. Note that the spectroscopic portion 15 may be arranged between the illuminating portion 11 and the measurement point, for example, in front of the illuminating portion 11, and may spectrally separate an illuminating light beam as the incident light and emit it to the illumination optical system 12.

The spectroscopic portion 15 includes, for example, a filter portion and a driving portion. The filter portion is a device including a plurality of band-pass filters having different center wavelengths in a transmission wavelength band. The center wavelengths of the band-pass filters are set such that light is spectrally separated appropriately according to the predetermined optical characteristics to be obtained with the multi-angle optical characteristic measuring device M. For example, in a case where spectral reflectivity is measured by spectrally separating visible light having wavelengths of 400 nm to 700 nm every 20 nm, the filter portion includes 16 band-pass filters, that is, the first to sixteenth band-pass filters, and the center wavelengths of the first to sixteenth band-pass filters are set in the range of 400 nm to 700 nm at intervals of 20 nm. Note that the wavelength interval for spectroscopy is not limited to 20 nm, but is set appropriately according to the specification of the multi-angle optical characteristic measuring device M. In addition, for example, in a case where light is spectrally separated into XYZ tristimulus values, the filter portion includes three band-pass filters, that is, the first to third band-pass filters. The center wavelength of the first band-pass filter is set such that its spectral response is approximate to International Commission on Illumination (CIE) color-matching function $X(\lambda)$. The center wavelength of the second band-pass filter is set such that its spectral response is approximate to CIE color-matching function $Y(\lambda)$. The center wavelength of the third band-pass filter is set such that its spectral response is approximate to CIE color-matching function $Z(\lambda)$. It should be noted that the plurality of band-pass filters may include band-pass filters for calculating spectral reflectivity and band-pass filters for calculating tristimulus values. More specifically, the filter portion includes the plurality of band-pass filters, a filter holding member that holds the plurality of band-pass filters, and a rod-like (cylindrical rod) rotation shaft. The filter holding member is, for example, a circular plate having a plurality of through holes formed at regular intervals in the circumferential direction. The number of the plurality of through holes is equal to the number of the plurality of band-pass filters. The dimensions of each of the plurality of through holes depend on the dimensions (size) of each of the plurality of band-pass filters. The plurality of band-pass filters are fit into the plurality of through holes, and are bonded and fixed with, for example, an adhesive or the like. A through hole is formed in the center position of the filter holding member. The rotation shaft is inserted through the through hole. Teeth are machined on the peripheral surface of the filter holding member, forming a toothed wheel (gear). The driving portion is a device that is connected to the control processing portion 21 and drives the filter portion to select a band-pass filter for use in filtering measurement light beams from among the plurality of band-pass filters under the control of the control processing portion 21. More specifically, the driving portion includes a motor that is connected to the control processing portion 21 and generates driving force under the control of the control processing portion 21, and a gear mounted on the output shaft of the motor. The gear of the driving portion meshes with the gear formed on the peripheral surface of the filter holding member so that the driving force of the motor is transmitted to the filter holding member. As a result, the filter holding member is rotationally driven around the rotation shaft. The filter holding member is arranged between the second reflecting mirror 14 and the light receiving optical system 16 in front of (on the incident side or object side of) the light receiving optical system 16 such that the optical axis of each band-pass filter coincides with the optical axis of the light receiving optical system 16 and the two-dimensional detecting portion 17 each time the plurality of band-pass filters are sequentially rotated.

Note that the number of the plurality of through holes may be larger than the number of the plurality of band-pass filters. There may be a through hole in which no band-pass filter is fit. There may be a through hole in which transparent glass is fit. There may be a through hole in which an ND filter is fit. The driving portion may include a motor that drives the rotation shaft of the filter portion directly or via a reduction gear. In this case, the rotation shaft is fixed to the filter holding member. As described above, the spectroscopic portion 15 may be formed such that all the measurement light beams from the first reflecting mirrors 13 enter one band-pass filter. Alternatively, the spectroscopic portion 15 may be formed such that measurement light beams from the first reflecting mirrors 13 enter different band-pass filters.

The light receiving optical system 16 is one optical system that receives measurement light beams from the plurality of first reflecting mirrors 13 (13-1 to 13-6) via the second reflecting mirror 14 and the spectroscopic portion 15. In the present embodiment, the light receiving optical system 16 is imaging lenses including a focusing portion (not illustrated) and one or more optical lenses. The focusing portion is connected to the control processing portion 21, and focuses and defocuses the measurement light beams on the detection surface (light receiving surface) of the two-dimensional detecting portion 17 under the control of the control processing portion 21. The focusing portion is a first moving mechanism that moves, along the optical axis direction, one or more optical lenses for focusing and defocusing selected from among the one or more optical lenses in the light receiving optical system 16. The light receiving optical system 16 can use, for example, what is called camera imaging lenses (for example, entire-group (all-lens) extension type imaging lenses or inner focus type imaging lenses), and preferably can use imaging lenses with an aberration performance designed for a megapixel image sensor. Note that the focusing portion may be a second moving mechanism that moves the two-dimensional detecting portion 17 along the optical axis direction.

In the present embodiment, in order for the focusing portion to simultaneously focus measurement light beams from the plurality of first reflecting mirrors 13 (13-1 to 13-6) on the detection surface of the two-dimensional detecting portion 17, the plurality of first reflecting mirrors 13 (13-1 to 13-6), the light receiving optical system 16, and the two-dimensional detecting portion 17 are arranged such that the optical path lengths of the measurement light beams from the measurement point to the two-dimensional detecting portion 17 are equal to each other. In the present embodiment, since the second reflecting mirror 14 for bending the optical axis AX as described above is provided, the plurality of first reflecting mirrors 13 (13-1 to 13-6), the second reflecting mirror 14, the light receiving optical system 16, and the two-dimensional detecting portion 17 are arranged such that the optical path lengths are equal to each other. In a case where it is unnecessary for the focusing portion to simultaneously focus the measurement light beams on the detection surface of the two-dimensional detecting portion 17, but the focusing portion only needs to sequentially focus one or more of the measurement light beams on the detection surface of the two-dimensional detecting portion 17 to eventually focus the measurement light beams on the detection surface of the two-dimensional detecting portion 17, the plurality of first reflecting mirrors 13 (13-1 to 13-6), the second reflecting mirror 14, the light receiving optical system 16, and the two-dimensional detecting portion 17 may not be arranged such that the optical path lengths are equal to each other.

The two-dimensional detecting portion 17 is a device that is connected to the control processing portion 21 and detects measurement light beams received by the light receiving optical system 16 under the control of the control processing portion 21. For example, the two-dimensional detecting portion 17 is a charged coupled device (CCD) or complementary metal oxide semiconductor (CMOS) image sensor including, for example, a plurality of photoelectric conversion elements (pixels) arranged in a two-dimensional array in two directions that are linearly independent from each other (for example, two directions orthogonal to each other). The two-dimensional detecting portion 17 photoelectrically converts each measurement light beam by each of the plurality of photoelectric conversion elements, thereby generating an electric signal representing the intensity level of each measurement light beam for each of the plurality of photoelectric conversion elements (pixels). The two-dimensional detecting portion 17 then outputs, to the control processing portion 21, the electric signal (result of measurement of each measurement light beam) generated for each of the plurality of photoelectric conversion elements. Each of the band-pass filters of the spectroscopic portion 15 is sequentially selected so that it is located on the optical axis of the light receiving optical system 16, whereby the result of measurement of the measurement light beam corresponding to each of the band-pass filters is output from the two-dimensional detecting portion 17 to the control processing portion 21.

The input portion 23 is an instrument that is connected to the control processing portion 21 and inputs, to the multi-angle optical characteristic measuring device M, for example, various commands such as commands for measuring the subject SP and various data necessary for measurement such as an identifier of the subject. For example, the input portion 23 is a plurality of input switches with predetermined functions allocated, a numeric keypad, a keyboard, or the like. The output portion 24 is an instrument that is connected to the control processing portion 21 and outputs, under the control of the control processing portion 21, commands and data input from the input portion 23 and results of measurement of the subject SP measured with the multi-angle optical characteristic measuring device M (for example, the predetermined optical characteristics such as color information and brilliance). For example, the output portion 24 is a display device such as a CRT display, an LCD, and an organic EL display, a printing device such as a printer, or the like.

Note that the input portion 23 and the output portion 24 may constitute a touch panel. In the configuration of a touch panel, the input portion 23 is a position input device that detects and inputs operation positions using a resistive film technique, a capacitance technique, or the like, and the output portion 24 is a display device. The touch panel includes the position input device on the display surface of the display device. One or more input content candidates that can be input are displayed on the display device. In response to the user touching the display position of a desired input content, the position is detected by the position input device, and the display content displayed at the detected position is input to the multi-angle optical characteristic measuring device M as the user's operation input content. Such a touch panel enables the user to understand the input operation intuitively, making the multi-angle optical characteristic measuring device M easy for the user to handle.

The IF portion 25 is a circuit that is connected to the control processing portion 21 and exchanges data with an external instrument under the control of the control processing portion 21. For example, the IF portion 25 is an interface circuit based on RS-232C, which is a serial communication technique, an interface circuit based on the Bluetooth (registered trademark) standard, an interface circuit for infrared communication based on the infrared data association (IrDA) standard or the like, an interface circuit based on the universal serial bus (USB) standard, or the like. The IF portion 25 is a communication card or the like for wired or wireless communication, and may communicate with an external device such as a server device over a communication network such as an Ethernet environment (Ethernet is a registered trademark).

The storage portion 22 is a circuit that is connected to the control processing portion 21 and stores various predetermined programs and various predetermined data under the control of the control processing portion 21. The various predetermined programs include, for example, control processing programs such as a control program for controlling each of the portions 11, 15 to 17, and 21 to 25 of the multi-angle optical characteristic measuring device M in accordance with the function of each portion and an optical characteristic calculation program for obtaining the predetermined optical characteristics of the subject SP facing the measurement point based on the result of detection of each measurement light beam detected by the two-dimensional detecting portion 17. The various predetermined data include, for example, data necessary for obtaining the predetermined optical characteristics of the subject SP, such as the light receiving position (light receiving area, light receiving pixel area) of a measurement light beam from each of the plurality of first reflecting mirrors 13 on the two-dimensional detecting portion 17, a reference value R ($\lambda$, AS angle) obtained by measuring a white calibration plate with a known reflectance using the multi-angle optical characteristic measuring device M, and the identifier of the subject SP. The storage portion 22 includes, for example, a read only memory (ROM) which is a non-volatile storage element, an electrically erasable programmable read only memory (EEPROM) which is a rewritable non-volatile storage element, or the like. The storage portion 22 further includes a random access memory (RAM) or the like that serves as what is called a working memory for the control processing portion 21 in which data or like generated during the execution of the predetermined programs are stored.

The control processing portion 21 is a circuit for controlling each of the portions 11, 15 to 17, and 21 to 25 of the multi-angle optical characteristic measuring device M in accordance with the function of each portion, and obtaining the predetermined optical characteristics of a subject. The control processing portion 21 includes, for example, a central processing unit (CPU) and its peripheral circuits. The control processing programs are executed, whereby a control portion 211 and an optical characteristic calculation portion 212 are functionally included in the control processing portion 21.

The control portion 211 controls each of the portions 11, 15 to 17, and 21 to 25 of the multi-angle optical characteristic measuring device M in accordance with the function of each portion.

Based on the result of detection of each measurement light beam detected by the two-dimensional detecting portion 17, the optical characteristic calculation portion 212 obtains the predetermined optical characteristics of the subject SP facing the measurement point. In a case where each measurement light beam is defocused, for example, at infinity on the two-dimensional detecting portion 17 by the focusing portion, the optical characteristic calculation portion 212 calculates, as the predetermined optical characteristics, color information (for example, spectral reflectivity, tristimulus values, etc.) of the subject SP using a well-known information process based on the result of detection of each measurement light beam detected by the two-dimensional detecting portion 17. In a case where each measurement light beam is focused on the two-dimensional detecting portion 17 by the focusing portion, the optical characteristic calculation portion 212 calculates, as the predetermined optical characteristics, the brilliance (for example, the number of bright points due to glitter material reflection, the distribution of the size of the bright points, etc.) of the subject SP using a well-known information process based on the result of detection of each measurement light beam detected by the two-dimensional detecting portion 17.

Figure 9:
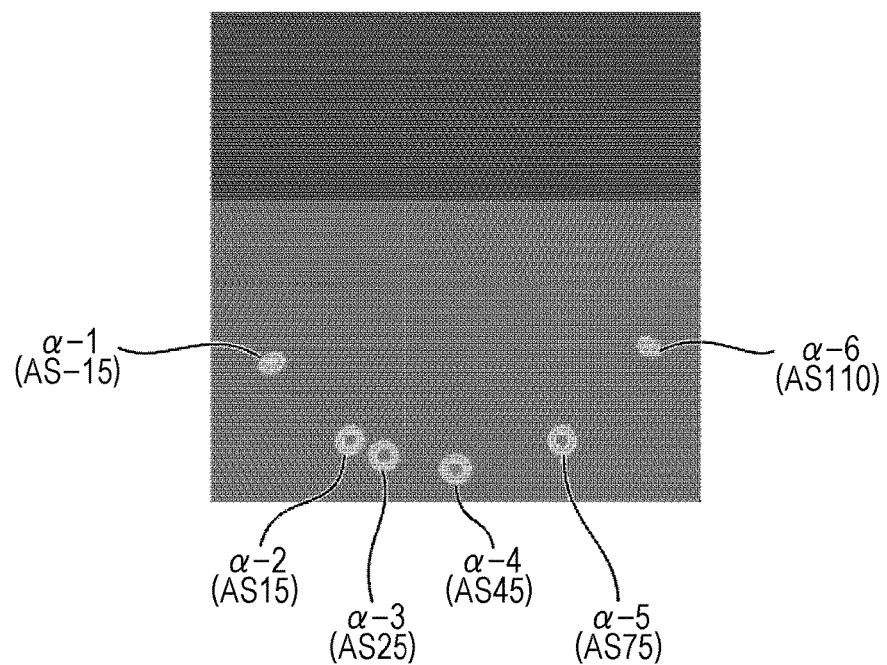
FIG. 9 is a diagram illustrating an example image of a measurement surface at each observation angle formed on a detection surface (light receiving surface) of a two-dimensional detecting portion when spectral reflectivity is measured with the multi-angle optical characteristic measuring device.
Figure 10:
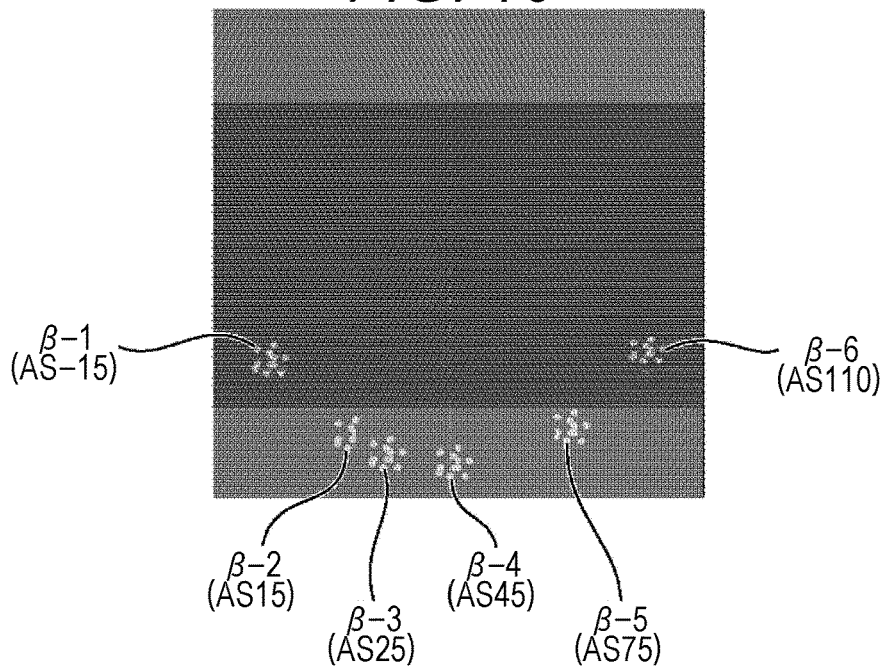
FIG. 10 is a diagram illustrating an example image of the measurement surface at each observation angle formed on the detection surface (light receiving surface) of the two-dimensional detecting portion when brilliance is measured with the multi-angle optical characteristic measuring device.
Figure 11:
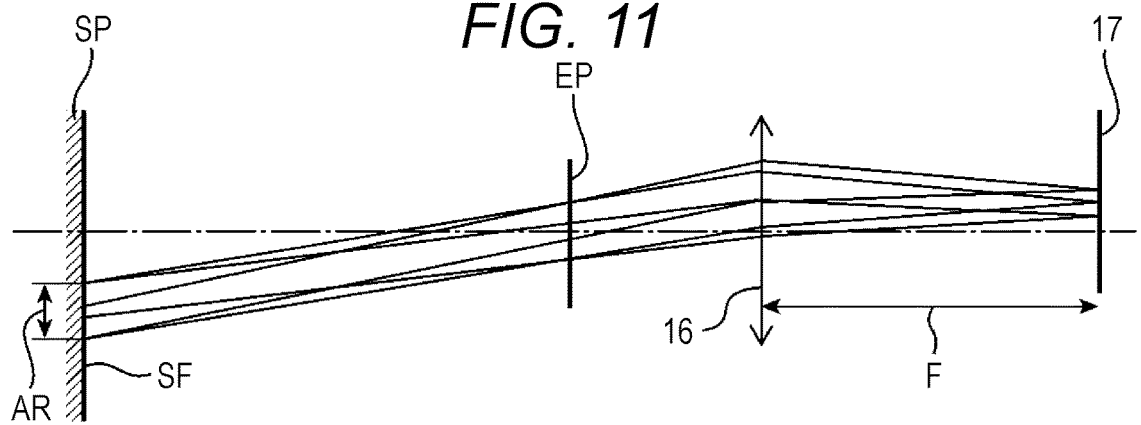
FIG. 11 is a diagram for explaining the conversion of each observation angle to a position on the two-dimensional detecting portion in the multi-angle optical characteristic measuring device.

Next, the operation of the multi-angle optical characteristic measuring device according to the present embodiment will be described. FIG. 9 is a diagram illustrating an example image of a measurement surface at each observation angle formed on the detection surface (light receiving surface) of the two-dimensional detecting portion when spectral reflectivity is measured with the multi-angle optical characteristic measuring device according to the embodiment. FIG. 10 is a diagram illustrating an example image of the measurement surface at each observation angle formed on the detection surface (light receiving surface) of the two-dimensional detecting portion when brilliance is measured with the multi-angle optical characteristic measuring device according to the embodiment. FIG. 11 is a diagram for explaining the conversion of each observation angle to a position on the two-dimensional detecting portion in the multi-angle optical characteristic measuring device according to the embodiment. In FIG. 11, the first reflecting mirror 13, the second reflecting mirror 14, and the spectroscopic portion 15 which have no optical power are not illustrated. Note that F represents the focal length of the light receiving optical system 16, EP represents the entrance pupil of the light receiving optical system 16, and AR represents the area of the aperture plane (measurement surface) of the measurement aperture AP.

In the multi-angle optical characteristic measuring device M having such a configuration, first, when the power switch (not illustrated) is turned on, the multi-angle optical characteristic measuring device M is activated. Each portion is initialized as necessary by the control processing portion 21. The control processing programs are executed, whereby the control portion 211 and the optical characteristic calculation portion 212 are functionally included in the control processing portion 21.

For example, in the case of measuring spectral reflectivity, the user (operator) sets the subject SP and the multi-angle optical characteristic measuring device M such that the bottom plate HSa faces the measurement surface SF of the subject SP, and inputs an instruction to start measuring the spectral reflectivity through the input portion 23. Note that the reference value R is measured in advance and stored in the storage portion 22.

In response to the input portion 23 accepting the instruction to start measuring the spectral reflectivity, the multi-angle optical characteristic measuring device M causes the control portion 211 of the control processing portion 21 to set the focusing portion in the light receiving optical system 16 to defocusing, for example, infinity. Next, the multi-angle optical characteristic measuring device M causes the control portion 211 of the control processing portion 21 to operate the spectroscopic portion 15 such that the optical axis of the first band-pass filter of the plurality of band-pass filters coincides with the optical axis of the light receiving optical system 16 and the two-dimensional detecting portion 17. Next, the multi-angle optical characteristic measuring device M causes the control portion 211 of the control processing portion 21 to operate the illuminating portion 11 such that an illuminating light beam is radiated. As a result, the illuminating portion 11 radiates an illuminating light beam.

As illustrated in FIG. 2, the illuminating light beam enters the illumination optical system 12 from the illuminating portion 11, is collimated by the illumination optical system 12, and irradiates the measurement surface SF of the subject SP through the measurement aperture AP. As illustrated in FIGS. 4 and 5, light beams derived from the radiated illuminating light beam and emitted from the measurement surface SF enter the 1a-th to 1f-th reflecting mirrors 13-1 to 13-6 as measurement light beams, and are reflected toward the second reflecting mirror 14. The second reflecting mirror 14 reflects each of the measurement light beams from the 1a-th to 1f-th reflecting mirrors 13-1 to 13-6 toward the entrance pupil of the light receiving optical system 16 through the spectroscopic portion 15. Each of the measurement light beams from the 1a-th to 1f-th reflecting mirrors 13-1 to 13-6 reflected by the second reflecting mirror 14 enters the first band-pass filter of the spectroscopic portion 15 and is filtered. The filtered measurement light beams from the 1a-th to 1f-th reflecting mirrors 13-1 to 13-6 pass through the light receiving optical system 16 and are received and detected at different light receiving positions (light receiving areas) on the detection surface (light receiving surface) of the two-dimensional detecting portion 17 as illustrated in FIG. 11. Angle information of a measurement light beam emitted from the measurement surface SF of the subject SP is separated with a resolution that depends on the aberration performance of the light receiving optical system 16, and converted to information of the light receiving position (light receiving area) on the detection surface (light receiving surface) of the two-dimensional detecting portion 17. The optical unit for a multi-angle optical characteristic measuring device according to the present embodiment can set a light receiving emission angle range for not only the measurement point but also a measurement surface having a certain area (small area). FIG. 9 illustrates example defocused images of the measurement surface SF derived from measurement light beams from the 1a-th to 1f-th reflecting mirrors 13-1 to 13-6 and formed on the detection surface of the two-dimensional detecting portion 17. In FIG. 9, image α-1 is the image of the measurement surface SF derived from the measurement light beam from the 1a-th reflecting mirror 13-1 arranged facing the measurement point at an observation angle of −15°. Image α-2 is the image of the measurement surface SF derived from the measurement light beam from the 1b-th reflecting mirror 13-2 arranged facing the measurement point at an observation angle +15°. Image α-3 is the image of the measurement surface SF derived from the measurement light beam from the 1c-th reflecting mirror 13-3 arranged facing the measurement point at an observation angle +25°. Image α-4 is the image of the measurement surface SF derived from the measurement light beam from the 1d-th reflecting mirror 13-4 arranged facing the measurement point at an observation angle +45°. Image α-5 is the image of the measurement surface SF derived from the measurement light beam from the 1e-th reflecting mirror 13-5 arranged facing the measurement point at an observation angle +75°. Image α-6 is the image of the measurement surface SF derived from the measurement light beam from the 1f-th reflecting mirror 13-6 arranged facing the measurement point at an observation angle +110°. As described above, different observation angles (light receiving angles) in the multi-angle geometry are converted to different light receiving positions (light receiving areas) on the detection surface (light receiving surface) of the two-dimensional detecting portion 17. The two-dimensional detecting portion 17 photoelectrically converts each of the received measurement light beams pixel by pixel, thereby generating an electric signal representing the intensity level of each of the measurement light beams for each pixel. The two-dimensional detecting portion 17 then outputs, to the control processing portion 21, the electric signal (result of measurement of each measurement light beam) generated for each pixel.

In response to acquiring the electric signal for each pixel from the two-dimensional detecting portion 17, the multi-angle optical characteristic measuring device M causes the optical characteristic calculation portion 212 of the control processing portion 21 to calculate the sum of pixel values for each of the light receiving positions (light receiving areas) corresponding to the measurement light beams from the 1a-th to 1f-th reflecting mirrors 13-1 to 13-6, and generate the results of measurement of the observation angles in the first band-pass filter S (1, ASn) (n=−15°, +15°, +25°, +45°, +75°, and +110°, that is, S (1, AS−15°), S (1, AS+15°), S (1, AS+25°), S (1, AS+45°), S (1, AS+75°), and S (1, AS+110°). Next, the multi-angle optical characteristic measuring device M causes the optical characteristic calculation portion 212 of the control processing portion 21 to divide each of the results of measurement of the observation angles S (1, ASn) by the reference value R (1, ASn) to calculate the spectral reflectivity S (1, ASn)/R (1, ASn) of each observation angle, that is, S (1, AS−15°)/R (1, AS−15°), S (1, AS+15°)/R (1, AS+15°), S (1, AS+25°)/R (1, AS+25°), S (1, AS+45°)/R (1, AS+45°), S (1, AS+75°)/R (1, AS+75°), and S (1, AS+110°)/R (1, AS+110°). The optical characteristic calculation portion 212 of the control processing portion 21 then stores them in the storage portion 22 in association with the center wavelength of the first band-pass filter.

In response to calculating the spectral reflectivity S (1, ASn)/R (1, ASn) of each observation angle in the first band-pass filter, the multi-angle optical characteristic measuring device M causes the control portion 211 of the control processing portion 21 to operate the spectroscopic portion 15 such that the optical axis of the second band-pass filter of the plurality of band-pass filters coincides with the optical axis of the light receiving optical system 16 and the two-dimensional detecting portion 17. Then, the multi-angle optical characteristic measuring device M operates in the same manner as when using the above-described first band-pass filter. The multi-angle optical characteristic measuring device M thus calculates the spectral reflectivity S (2, ASn)/R (2, ASn) of each observation angle in the second band-pass filter, and stores them in the storage portion 22. Thereafter, similarly, the multi-angle optical characteristic measuring device M calculates the spectral reflectivity S (k, ASn)/R (k, ASn) of each observation angle in the third to sixteenth band-pass filters, and stores them in the storage portion 22 (k=integer of 1 to 16, n=−15°, +15°, +25°, +45°, +75°, and +110°).

Then, in response to calculating the spectral reflectivity S (k, ASn)/R (k, ASn) of each observation angle in all of the first to sixteenth band-pass filters, the multi-angle optical characteristic measuring device M causes the control portion 211 of the control processing portion 21 to output the spectral reflectivity S (k, ASn)/R (k, ASn) of each observation angle stored in the storage portion 22 to the output portion 24 and to the IF portion 25 as necessary.

In this manner, the spectral reflectivity of the subject SP is measured as color information. Note that the multi-angle optical characteristic measuring device M may measure tristimulus values as color information using tristimulus value band-pass filters.

For example, in the case of measuring brilliance, the user (operator) sets the subject SP and the multi-angle optical characteristic measuring device M such that the bottom plate HSa faces the measurement surface SF of the subject SP, and inputs an instruction to start measuring the brilliance through the input portion 23.

In response to the input portion 23 accepting the instruction to start measuring the brilliance, the multi-angle optical characteristic measuring device M causes the control portion 211 of the control processing portion 21 to set the focusing portion to focusing. Next, the multi-angle optical characteristic measuring device M causes the control portion 211 of the control processing portion 21 to operate the spectroscopic portion 15 such that the optical axis of the first band-pass filter of the plurality of band-pass filters coincides with the optical axis of the light receiving optical system 16 and the two-dimensional detecting portion 17. In a case where spectroscopy is unnecessary, the control portion 211 operates the spectroscopic portion 15 such that the optical axis of a through hole of the filter portion in which no band-pass filter is fit or the optical axis of a through hole of the filter portion in which transparent glass is fit coincides with the optical axis of the light receiving optical system 16 and the two-dimensional detecting portion 17. Next, the multi-angle optical characteristic measuring device M causes the control portion 211 of the control processing portion 21 to operate the illuminating portion 11 such that an illuminating light beam is radiated. As a result, the illuminating portion 11 radiates an illuminating light beam.

Thereafter, the multi-angle optical characteristic measuring device M operates in the same manner as when measuring the spectral reflectivity. Consequently, focused images of the measurement surface SF derived from the measurement light beams from the 1a-th to 1f-th reflecting mirrors 13-1 to 13-6 are formed on the detection surface (light receiving surface) of the two-dimensional detecting portion 17. Examples of such images are illustrated in FIG. 10. In FIG. 10, image β-1 is the image of the measurement surface SF derived from the measurement light beam from the 1a-th reflecting mirror 13-1 arranged facing the measurement point at an observation angle of −15°. Image β-2 is the image of the measurement surface SF derived from the measurement light beam from the 1b-th reflecting mirror 13-2 arranged facing the measurement point at an observation angle +15°. Image β-3 is the image of the measurement surface SF derived from the measurement light beam from the 1c-th reflecting mirror 13-3 arranged facing the measurement point at an observation angle +25°. Image β-4 is the image of the measurement surface SF derived from the measurement light beam from the 1d-th reflecting mirror 13-4 arranged facing the measurement point at an observation angle +45°. Image β-5 is the image of the measurement surface SF derived from the measurement light beam from the 1e-th reflecting mirror 13-5 arranged facing the measurement point at an observation angle +75°. Image β-6 is the image of the measurement surface SF derived from the measurement light beam from the 1f-th reflecting mirror 13-6 arranged facing the measurement point at an observation angle +110°. As described above, different observation angles (light receiving angles) in the multi-angle geometry are converted to different light receiving positions (light receiving areas) on the detection surface (light receiving surface) of the two-dimensional detecting portion 17. The two-dimensional detecting portion 17 photoelectrically converts each of the received measurement light beams pixel by pixel, thereby generating an electric signal representing the intensity level of each of the measurement light beams for each pixel. The two-dimensional detecting portion 17 then outputs, to the control processing portion 21, the electric signal (result of measurement of each measurement light beam) generated for each pixel.

In response to acquiring the electric signal for each pixel from the two-dimensional detecting portion 17, the multi-angle optical characteristic measuring device M causes the optical characteristic calculation portion 212 of the control processing portion 21 to calculate the number of bright points or the distribution of the size of the bright points for each of the light receiving positions (light receiving areas) corresponding to the measurement light beams from the 1a-th to 1f-th reflecting mirrors 13-1 to 13-6. The optical characteristic calculation portion 212 of the control processing portion 21 then stores them in the storage portion 22.

If it is necessary to measure brilliance using spectroscopy, the multi-angle optical characteristic measuring device M operates in the same way as above by sequentially using the second to eighth band-pass filters, calculates the number of bright points or the distribution of the size of the bright points for each band-pass filter, and stores them in the storage portion 22.

The multi-angle optical characteristic measuring device M then causes the control portion 211 of the control processing portion 21 to output the number of bright points or the distribution of the size of the bright points for each observation angle stored in the storage portion 22 to the output portion 24 and to the IF portion 25 as necessary.

In this manner, the number of bright points on the subject SP or the distribution of the size of the bright points is measured as brilliance.

As described above, in the multi-angle optical characteristic measuring device M and the optical unit for a multi-angle optical characteristic measuring device used in the multi-angle optical characteristic measuring device M according to the embodiment, the plurality of first reflecting mirrors 13 (13-1 to 13-6) are used for modifying the traveling directions of measurement light beams emitted from the measurement point in response to an illuminating light beam, instead of a toroidal mirror or a conical mirror.

Therefore, the traveling direction of a measurement light beam at each observation angle (light receiving angle) in the multi-angle geometry can be simply adjusted independently for each of the plurality of first reflecting mirrors 13, facilitating assembly and adjustment thereof. As described above, since neither a toroidal mirror nor a conical mirror is used in the multi-angle optical characteristic measuring device M and the optical unit for a multi-angle optical characteristic measuring device, cost can be reduced. Therefore, the multi-angle optical characteristic measuring device M and the optical unit for a multi-angle optical characteristic measuring device can facilitate assembly and adjustment of multi-angle geometry and reduce cost.

In the multi-angle optical characteristic measuring device M and the optical unit for a multi-angle optical characteristic measuring device, the plurality of first reflecting mirrors 13 modify the traveling directions of measurement light beams such that the two-dimensional detecting portion 17 detects the measurement light beams at different positions on the two-dimensional detecting portion 17. Therefore, the multi-angle optical characteristic measuring device M and the optical unit for a multi-angle optical characteristic measuring device convert each observation angle in the multi-angle geometry to each position on the two-dimensional detecting portion 17. Thus, the multi-angle optical characteristic measuring device M and the optical unit for a multi-angle optical characteristic measuring device can capture measurement light beams at the respective observation angles in the multi-angle geometry with one light receiving optical system, and can intensively detect (measure) the measurement light beams in one image. Therefore, the multi-angle optical characteristic measuring device M and the optical unit for a multi-angle optical characteristic measuring device can be downsized.

Since the multi-angle optical characteristic measuring device M and the optical unit for a multi-angle optical characteristic measuring device further include the spectroscopic portion 15, it is possible to measure reflectance and the like for each wavelength or wavelength band, and it is possible to calculate color information such as spectral reflectivity and tristimulus values as an example of the predetermined optical characteristics.

The multi-angle optical characteristic measuring device M and the optical unit for a multi-angle optical characteristic measuring device further include the focusing portion. Therefore, when defocusing is set by the focusing portion, color information such as spectral reflectivity and tristimulus values can be calculated as an example of the predetermined optical characteristics. In contrast, when focusing is set by the focusing portion, brilliance such as the number of bright points and the distribution of the size of bright points can be calculated as another example of the predetermined optical characteristics.

In this manner, the multi-angle optical characteristic measuring device M and the optical unit for a multi-angle optical characteristic measuring device can measure the color information and brilliance of a subject with the same optical system, and can further measure brilliance at a plurality of angles.

In the multi-angle optical characteristic measuring device M and the optical unit for a multi-angle optical characteristic measuring device, the optical path lengths of the measurement light beams from the measurement point to the two-dimensional detecting portion 17 are equal to each other. Therefore, the measurement light beams can be focused simultaneously by the two-dimensional detecting portion 17, and the focused measurement light beams can be detected simultaneously by the two-dimensional detecting portion 17.

Since the multi-angle optical characteristic measuring device M and the optical unit for a multi-angle optical characteristic measuring device further include the second reflecting mirror 14, the light receiving optical system 16 can be arranged above the measurement point (in the present embodiment, the central position CP1 of the aperture plane (measurement surface) of the measurement aperture AP), and downsizing can be achieved.

In the multi-angle optical characteristic measuring device M and the optical unit for a multi-angle optical characteristic measuring device, the plurality of first reflecting mirrors 13 are arranged at an equal distance from the measurement point, and modify the traveling directions of the measurement light beams toward the entrance pupil of the light receiving optical system 16 which is the point of focusing (converging) of light beams from all the angles of view. Therefore, the measurement light beams from the plurality of reflecting mirrors 13 can be more accurately focused on the two-dimensional detecting portion 17, so that clear images can be obtained.

In the above description, the multi-angle optical characteristic measuring device M may correct the optical characteristics using the double-pass correction process disclosed in Japanese Patent No. 5737390, for example. This makes it possible to more accurately measure the optical characteristics even when the multi-angle optical characteristic measuring device M is inclined with respect to the subject SP or in a case where the measurement surface SF of the subject SP is curved. The multi-angle optical characteristic measuring device M using the double-pass correction process includes a first illuminating portion, a second illuminating portion, a first light receiving portion, and a second light receiving portion for each geometry of the multi-angle geometry. The first illuminating portion radiates, at a predetermined first incident angle with respect to a predetermined reference line (for example, the normal n) intersecting with the aperture plane of the measurement aperture AP, a first illuminating light beam toward the point of intersection (for example, the measurement point) between the aperture plane and the reference line. The second illuminating portion is exactly opposite to a first arrangement position of the first illuminating portion with respect to the reference line and is symmetrical to the first illuminating portion across the reference line. The second illuminating portion radiates a second illuminating light beam toward the points of intersection. The first light receiving portion is arranged on a plane including the first arrangement position of the first illuminating portion, the reference line, and a second arrangement position of the second illuminating portion. The first light receiving portion faces the point of intersection at a predetermined first observation angle with respect to the reference line to receive light from the point of intersection. The second light receiving portion is symmetrical to the first light receiving portion across the reference line on the plane. The second light receiving portion receives light from the point of intersection. The multi-angle optical characteristic measuring device M calculates the predetermined optical characteristics of the measurement target at the point of intersection based on a first measurement value provided by the first light receiving portion and a second measurement value provided by the second light receiving portion.

Figure 12:
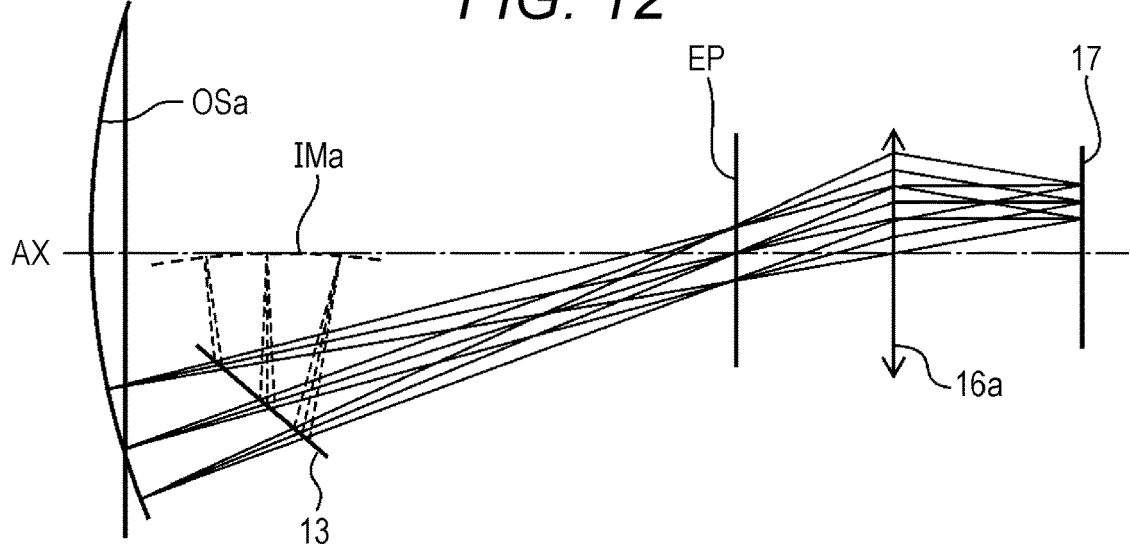
FIG. 12 is an optical path diagram for explaining a focusing range for a light receiving optical system designed to include a spherical surface as its object surface, according to a modification.

In the above description, an object surface of the light receiving optical system 16 that is a conjugate surface of the two-dimensional detecting portion 17 may be a spherical surface centered at the intersection of the entrance pupil and the optical axis of the light receiving optical system 16. That is, the multi-angle optical characteristic measuring device M and the optical unit for a multi-angle optical characteristic measuring device may include a light receiving optical system 16a formed (designed) as illustrated in FIG. 12, in place of the light receiving optical system 16. An object surface OSa of the light receiving optical system 16a that is a conjugate surface of the two-dimensional detecting portion 17 is a spherical surface centered at the intersection of the entrance pupil EP and the optical axis AX of the light receiving optical system 16a.

Figure 13:
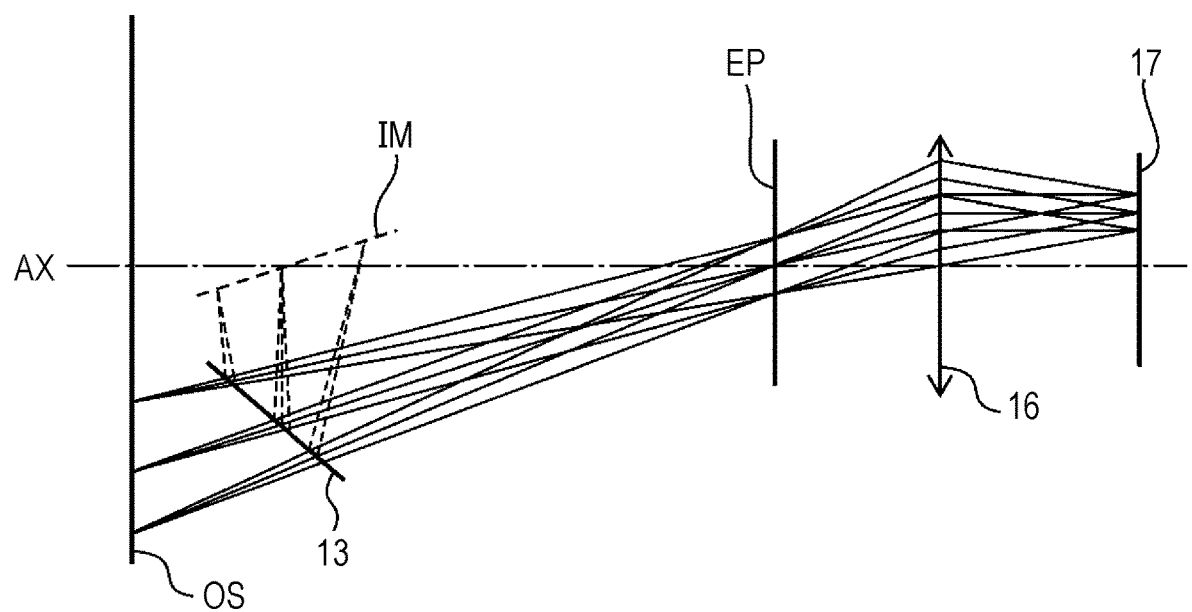
FIG. 13 is an optical path diagram for explaining a focusing range for a light receiving optical system designed to include a plane as its object surface, in contrast with the configuration illustrated in FIG. 12.

FIG. 12 is an optical path diagram for explaining a focusing range for a light receiving optical system designed to include a spherical surface as its object surface, according to a modification. FIG. 13 is an optical path diagram for explaining a focusing range for a light receiving optical system designed to include a plane as its object surface, in contrast with the configuration illustrated in FIG. 12. In FIGS. 12 and 13, the second reflecting mirror 14 and the spectroscopic portion 15 which have no optical power are not illustrated.

As illustrated in FIG. 13, in a case where the multi-angle optical characteristic measuring device M and the optical unit for a multi-angle optical characteristic measuring device include the light receiving optical system 16 formed (designed) to include a plane as an object surface OS of the light receiving optical system 16 that is a conjugate surface of the two-dimensional detecting portion 17, as illustrated in FIG. 13, images formed on an image surface IM by the plurality of first reflecting mirrors 13 may be blurred on their peripheries when the light receiving optical system 16 is in focus since the image surface IM is a plane. However, in a case where the light receiving optical system 16a formed (designed) to include a spherical surface centered at the intersection of the entrance pupil EP and the optical axis AX as the object surface OSa is used as in this modification, as illustrated in FIG. 12, images formed on an image surface IMa by the plurality of first reflecting mirrors 13 are unlikely to be blurred on their peripheries when the light receiving optical system 16 is in focus since the image surface IMa is a spherical surface. Therefore, the multi-angle optical characteristic measuring device M and the optical unit for a multi-angle optical characteristic measuring device according to this modification can focus on a wider surface (measurement surface) including the measurement point.

In the above description, the multi-angle optical characteristic measuring device M and the optical unit for a multi-angle optical characteristic measuring device may further include a branching portion. The branching portion causes part of an illuminating light beam to branch off as a branch light beam. The branching portion is arranged between the illuminating portion 11 and the measurement point such that the branch light beam is detected by the two-dimensional detecting portion 17. Preferably, the branching portion is arranged such that the branch light beam is detected by the two-dimensional detecting portion 17 via the light receiving optical system 16. Further preferably, the branching portion is arranged such that the branch light beam is detected by the two-dimensional detecting portion 17 via the second reflecting mirror 14 and the light receiving optical system 16. For example, the branching portion includes a beam splitter 20 that reflects part of incident light and transmits the rest (for example, transmitted light amount:reflected light amount=95:5, transmitted light amount:reflected light amount=90:10, or the like). As indicated by the broken lines in FIG. 2, in the same manner as the first reflecting mirror 13, the beam splitter 20 is arranged on the optical axis of the illumination optical system 12 such that the optical axis of the beam splitter 20 coincides with the generatrix of the cone CC and that a third arrangement position CP3 of the beam splitter 20 is located on the intersection line BL between the reference plane RP and the side surface of the cone CC. The third arrangement position CP3 is the position of the intersection of the beam splitter surface and the optical axis of the beam splitter 20. In this case, the optical characteristic calculation portion 212 is formed to obtain the optical characteristics further based on a second result of detection of the branch light beam detected by the two-dimensional detecting portion 17. For example, the optical characteristic calculation portion 212 obtains the optical characteristics in consideration of the fluctuation of the illuminating light beam (that is, optical characteristics obtained by correcting the fluctuation of the illuminating light beam). Note that illustration of the beam splitter 20 by broken lines is omitted from FIGS. 3 to 5.

Since the multi-angle optical characteristic measuring device M and the optical unit for a multi-angle optical characteristic measuring device further include the branching portion (in the above example, the beam splitter 20), an illuminating light beam can be monitored by the two-dimensional detecting portion 17, and the optical characteristics can be obtained in consideration of the illuminating light beam actually radiated to the subject SP facing the measurement point.

In the above description, as can be understood from FIGS. 9 and 10, there is a space on the detection surface (light receiving surface) of the two-dimensional detecting portion 17 between images of measurement light beams from the respective observation angles, and light for other images can be received in this space. For this reason, the multi-angle optical characteristic measuring device M and the optical unit for a multi-angle optical characteristic measuring device in the above description can further include the first reflecting mirrors 13 at other observation angles (light receiving angles) in addition to the six 1a-th to 1f-th reflecting mirrors 13-1 to 13-6. For example, the first reflecting mirrors 13 can further be arranged at an angle between observation angle +25° and observation angle +45°, an angle between observation angle 0° and observation angle −15°, an angle between observation angle 0° and observation angle +15°, and the like. The multi-angle optical characteristic measuring device M and the optical unit for a multi-angle optical characteristic measuring device formed as described above can obtain data from a larger number of observation angles (light receiving angles) simply with additional first reflecting mirrors 13.

In the above description, the multi-angle optical characteristic measuring device M and the optical unit for a multi-angle optical characteristic measuring device measure brilliance using the illuminating portion 11. Alternatively, in the above description, the multi-angle optical characteristic measuring device M and the optical unit for a multi-angle optical characteristic measuring device may further include a second illuminating portion 18 and a second illumination optical system 19 as indicated by the broken lines in FIG. 3. The second illuminating portion 18 irradiates the measurement point with a second illuminating light beam for brilliance measurement which is used for measuring brilliance. The second illumination optical system 19 collimates (makes parallel) the second illuminating light beam emitted from the second illuminating portion 18 and guides it to the measurement point. In such a case, the second illumination optical system 19 may be arranged on the reference plane RP. Alternatively, as illustrated by the broken lines in FIG. 3, the second illumination optical system 19 may guide the second illuminating light beam to the measurement point at a predetermined angle with respect to the reference plane RP (at a position offset from the reference plane RP).

The present specification has disclosed the techniques of various aspects as described above. Below is a summary of the main techniques.

An optical unit for a multi-angle optical characteristic measuring device according to an aspect includes: an illuminating portion that irradiates a predetermined measurement point on a measurement surface with an illuminating light beam; a plurality of reflecting mirrors that are arranged facing the measurement point at a plurality of different observation angles, and modify traveling directions of measurement light beams emitted from the measurement point in response to the illuminating light beam; one light receiving optical system that receives the measurement light beams from the plurality of reflecting mirrors; and a two-dimensional detecting portion that detects the measurement light beams received by the light receiving optical system, and the plurality of reflecting mirrors modifies the traveling directions of the measurement light beams such that the two-dimensional detecting portion detects the measurement light beams at different positions on the two-dimensional detecting portion. Preferably, in the optical unit for a multi-angle optical characteristic measuring device, each of the plurality of reflecting mirrors does not have a focal point (converging point) of a measurement light beam between the measurement point and the incident surface of the light receiving optical system. Preferably, in the optical unit for a multi-angle optical characteristic measuring device, each of the plurality of reflecting mirrors is a plane mirror having no optical power. The optical power is also called refracting power and is the reciprocal of the focal length in air having a refractive index of 1. Preferably, in the optical unit for a multi-angle optical characteristic measuring device, each of the plurality of reflecting mirrors is arranged on a virtual reference plane including the normal of the measurement surface passing through the measurement point and the optical axis of the illuminating portion.

In such an optical unit for a multi-angle optical characteristic measuring device, the plurality of reflecting mirrors is used for modifying the traveling directions of measurement light beams emitted from the measurement point of the measurement surface in response to an illuminating light beam, instead of a toroidal mirror or a conical mirror. Therefore, the traveling direction of a measurement light beam at each observation angle (light receiving angle) in the multi-angle geometry can be simply adjusted independently for each of the plurality of reflecting mirrors, facilitating assembly and adjustment thereof. Since neither a toroidal mirror nor a conical mirror is used in the optical unit for a multi-angle optical characteristic measuring device, cost can be reduced. Therefore, the optical unit for a multi-angle optical characteristic measuring device can facilitate assembly and adjustment of multi-angle geometry and reduce cost.

In the optical unit for a multi-angle optical characteristic measuring device, the plurality of reflecting mirrors modifies the traveling directions of measurement light beams such that the two-dimensional detecting portion detects the measurement light beams at different positions on the two-dimensional detecting portion. Therefore, the optical unit for a multi-angle optical characteristic measuring device converts each observation angle in the multi-angle geometry to each position on the two-dimensional detecting portion. Thus, the optical unit for a multi-angle optical characteristic measuring device can capture measurement light beams at the respective observation angles in the multi-angle geometry with one light receiving optical system, and can intensively detect (measure) the measurement light beams in one image. Therefore, the optical unit for a multi-angle optical characteristic measuring device can be downsized.

According to another aspect, the optical unit for a multi-angle optical characteristic measuring device further includes a spectroscopic portion between the illuminating portion and the two-dimensional detecting portion, and the spectroscopic portion spectrally separates the illuminating light beam or the measurement light beams. Preferably, in the optical unit for a multi-angle optical characteristic measuring device, the spectroscopic portion is arranged between the illuminating portion and the measurement point, for example, in front of the illuminating portion, and spectrally separates the illuminating light beam. Preferably, in the optical unit for a multi-angle optical characteristic measuring device, the spectroscopic portion is arranged between the measurement point and the two-dimensional detecting portion, for example, in front of the light receiving optical system, and spectrally separates the measurement light beams. Preferably, in the optical unit for a multi-angle optical characteristic measuring device, the spectroscopic portion includes a plurality of band-pass filters having different center wavelengths in a transmission wavelength band.

Since the optical unit for a multi-angle optical characteristic measuring device further includes the spectroscopic portion, it is possible to measure reflectance and the like for each wavelength or wavelength band, and it is possible to calculate color information such as spectral reflectivity and tristimulus values as an example of the predetermined optical characteristics.

According to another aspect, the optical unit for a multi-angle optical characteristic measuring device further includes a focusing portion that focuses and defocuses each of the measurement light beams at the two-dimensional detecting portion. Preferably, in the optical unit for a multi-angle optical characteristic measuring device, the light receiving optical system includes one or more optical lenses, and the focusing portion is a first moving mechanism that moves, along the optical axis direction, an optical lens for focusing and defocusing selected from among the one or more optical lenses in the light receiving optical system. Preferably, in the optical unit for a multi-angle optical characteristic measuring device, the focusing portion is a second moving mechanism that moves the two-dimensional detecting portion along the optical axis direction.

Such an optical unit for a multi-angle optical characteristic measuring device further includes the focusing portion. Therefore, when defocusing is set by the focusing portion, color information such as spectral reflectivity and tristimulus values can be calculated as an example of the predetermined optical characteristics based on the result of detection of each measurement light beam detected by the two-dimensional detecting portion. In contrast, when focusing is set by the focusing portion, brilliance such as the number of bright points and the distribution of the size of bright points can be calculated as another example of the predetermined optical characteristics based on the result of detection of each measurement light beam detected by the two-dimensional detecting portion.

According to another aspect, in the optical unit for a multi-angle optical characteristic measuring device, the plurality of reflecting mirrors, the light receiving optical system, and the two-dimensional detecting portion are arranged such that optical path lengths of the measurement light beams from the measurement point to the two-dimensional detecting portion are equal to each other.

In such an optical unit for a multi-angle optical characteristic measuring device, measurement light beams from the plurality of reflecting mirrors can be focused simultaneously by the two-dimensional detecting portion, and the focused measurement light beams can be detected simultaneously by the two-dimensional detecting portion.

According to another aspect, in the optical unit for a multi-angle optical characteristic measuring device, an object surface of the light receiving optical system that is a conjugate surface of the two-dimensional detecting portion is a spherical surface centered at an intersection of an entrance pupil and an optical axis of the light receiving optical system.

In such an optical unit for a multi-angle optical characteristic measuring device, the object surface of the light receiving optical system that is the conjugate surface of the two-dimensional detecting portion is a spherical surface centered at the intersection of the entrance pupil and the optical axis of the light receiving optical system. Therefore, the optical axis of each observation angle is perpendicular to the conjugate object surface, and the focusing portion can focus on a wider surface (measurement surface) including the measurement point.

According to another aspect, in the optical unit for a multi-angle optical characteristic measuring device, each of the plurality of reflecting mirrors is arranged on a virtual reference plane including a normal of the measurement surface passing through the measurement point and an optical axis of the illuminating portion, the light receiving optical system is arranged above the measurement point, the optical unit further includes a second reflecting mirror that modifies the traveling directions of the measurement light beams from the plurality of reflecting mirrors toward the light receiving optical system, and in a case where the second reflecting mirror is not provided, the light receiving optical system is arranged at an arrangement position where the optical axis of the light receiving optical system coincides with a virtual perpendicular line passing through the measurement point and orthogonal to the reference plane.

Since such an optical unit for a multi-angle optical characteristic measuring device further includes the second reflecting mirror, the light receiving optical system can be arranged above the measurement point, and downsizing can be achieved.

According to another aspect, in the optical unit for a multi-angle optical characteristic measuring device, the plurality of reflecting mirrors is arranged at an equal distance from the measurement point, and modify the traveling directions of the measurement light beams toward an entrance pupil of the light receiving optical system.

In such an optical unit for a multi-angle optical characteristic measuring device, the plurality of reflecting mirrors modifies the traveling directions of the measurement light beams toward the entrance pupil which is the point of focusing (converging) of light beams from all the angles of view. Therefore, the measurement light beams from the plurality of reflecting mirrors can be more accurately focused on the two-dimensional detecting portion, so that clear images can be obtained.

According to another aspect, the optical unit for a multi-angle optical characteristic measuring device further includes a branching portion that causes part of the illuminating light beam to branch off as a branch light beam, and the branching portion is arranged between the illuminating portion and the measurement point such that the branch light beam is detected by the two-dimensional detecting portion. The optical characteristic calculation portion obtains the optical characteristics further based on a second result of detection of the branch light beam detected by the two-dimensional detecting portion. Preferably, in the optical unit for a multi-angle optical characteristic measuring device, the branching portion is arranged such that the branch light beam is detected by the two-dimensional detecting portion via the light receiving optical system. Preferably, in the optical unit for a multi-angle optical characteristic measuring device, the branching portion is arranged such that the branch light beam is detected by the two-dimensional detecting portion via the second reflecting mirror and the light receiving optical system.

Since such an optical unit for a multi-angle optical characteristic measuring device includes the branching portion, an illuminating light beam can be monitored by the two-dimensional detecting portion, and the optical characteristics can be obtained in consideration of the illuminating light beam actually radiated to the subject facing the measurement point. For example, the multi-angle optical characteristic measuring device can obtain the optical characteristics in consideration of the fluctuation of the illuminating light beam (that is, optical characteristics obtained by correcting the fluctuation of the illuminating light beam).

A multi-angle optical characteristic measuring device according to another aspect includes: the optical unit for a multi-angle optical characteristic measuring device according to any of the above aspects; and an optical characteristic calculation portion that obtains predetermined optical characteristics of a subject facing the measurement point based on results of detection of the measurement light beams detected by the two-dimensional detecting portion. Preferably, in the multi-angle optical characteristic measuring device including the focusing portion, in a case where each measurement light beam is defocused on the two-dimensional detecting portion by the focusing portion, the optical characteristic calculation portion calculates, as the predetermined optical characteristics, color information of the subject facing the measurement point based on the result of detection of each measurement light beam detected by the two-dimensional detecting portion. Preferably, in the optical unit for a multi-angle optical characteristic measuring device including the focusing portion, in a case where each measurement light beam is focused on the two-dimensional detecting portion by the focusing portion, the optical characteristic calculation portion calculates, as the predetermined optical characteristics, the brilliance of the subject facing the measurement point based on the result of detection of each measurement light beam detected by the two-dimensional detecting portion.

Such a multi-angle optical characteristic measuring device includes the optical unit for a multi-angle optical characteristic measuring device according to any of the above aspects, and thus can facilitate assembly and adjustment of multi-angle geometry and reduce cost.

This application is based on Japanese Patent Application No. 2016-165570 filed on Aug. 26, 2016, including the specification, claims, drawings, and abstract, the entire disclosure of which is incorporated herein by reference in its entirety.

Although embodiments of the present invention have been illustrated and described in detail, it is to be understood that these are merely example drawings and example cases, and the present invention is not limited to them. The scope of the present invention should be construed according to the terms in the appended claims.

In order to express the present invention, the present invention has been described appropriately and fully so far through the embodiments with reference to the drawings. Those skilled in the art should understand that modifications and/or improvements can be easily made to the above embodiments. Therefore, as long as modified forms or improved forms made by those skilled in the art do not depart from the scope of the claims, the modified forms or improved forms are construed as being included in the scope of the claims.

INDUSTRIAL APPLICABILITY

The present invention can provide an optical unit for a multi-angle optical characteristic measuring device and a multi-angle optical characteristic measuring device using the same.

The invention claimed is:

1. An optical unit for a multi-angle optical characteristic measuring device comprising:
    an illuminating part that irradiates a predetermined measurement point on a measurement surface with an illuminating light beam in a single direction;
    a plurality of reflecting mirrors that are arranged facing the measurement point at a plurality of different observation angles, and modify traveling directions of measurement light beams emitted from the measurement point in response to the illuminating light beam;
    one light receiving optical system that receives the measurement light beams from the plurality of reflecting mirrors; and
    a two-dimensional detecting part that detects the measurement light beams received by the light receiving optical system, wherein
    the plurality of reflecting mirrors modifies the traveling directions of the measurement light beams such that the two-dimensional detecting part detects the measurement light beams at different positions on the two-dimensional detecting part.

2. The optical unit for a multi-angle optical characteristic measuring device according to claim 1, further comprising a spectroscopic part between the illuminating part and the two-dimensional detecting part, the spectroscopic part spectrally separating the illuminating light beam or the measurement light beams.

3. The optical unit for a multi-angle optical characteristic measuring device according to claim 1, further comprising a focusing part that focuses and defocuses each of the measurement light beams at the two-dimensional detecting part.

4. The optical unit for a multi-angle optical characteristic measuring device according to claim 3, wherein
    the plurality of reflecting mirrors, the light receiving optical system, and the two-dimensional detecting part are arranged such that optical path lengths of the measurement light beams from the measurement point to the two-dimensional detecting part are equal to each other.

5. The optical unit for a multi-angle optical characteristic measuring device according to claim 4, wherein
    an object surface of the light receiving optical system that is a conjugate surface of the two-dimensional detecting part is a spherical surface centered at an intersection of an entrance pupil and an optical axis of the light receiving optical system.

6. The optical unit for a multi-angle optical characteristic measuring device according to claim 1, wherein
    each of the plurality of reflecting mirrors is arranged on a virtual reference plane including a normal of the measurement surface passing through the measurement point and an optical axis of the illuminating part,
    the light receiving optical system is arranged above the measurement point,
    the optical unit further includes a second reflecting mirror that modifies the traveling directions of the measurement light beams from the plurality of reflecting mirrors toward the light receiving optical system, and
    in a case where the second reflecting mirror is not provided, the light receiving optical system is arranged at an arrangement position where the optical axis of the light receiving optical system coincides with a virtual perpendicular line passing through the measurement point and orthogonal to the reference plane.

7. The optical unit for a multi-angle optical characteristic measuring device according to claim 6, wherein
    the plurality of reflecting mirrors is arranged at an equal distance from the measurement point, and modifies the traveling directions of the measurement light beams toward the entrance pupil of the light receiving optical system.

8. The optical unit for a multi-angle optical characteristic measuring device according to claim 1, further comprising
    a branching part that causes part of the illuminating light beam to branch off as a branch light beam, the branching part being arranged between the illuminating part and the measurement point such that the branch light beam is detected by the two-dimensional detecting part, wherein
    a hardware processor obtains optical characteristics further based on a second result of detection of the branch light beam detected by the two-dimensional detecting part.

9. A multi-angle optical characteristic measuring device comprising:
    the optical unit for a multi-angle optical characteristic measuring device according to claim 1; and
    a hardware processor that obtains predetermined optical characteristics of a subject facing the measurement point based on results of detection of the measurement light beams detected by the two-dimensional detecting part.

10. The optical unit for a multi-angle optical characteristic measuring device according to claim 2, further comprising
    a focusing part that focuses and defocuses each of the measurement light beams at the two-dimensional detecting part.

11. The optical unit for a multi-angle optical characteristic measuring device according to claim 2, wherein
    each of the plurality of reflecting mirrors is arranged on a virtual reference plane including a normal of the measurement surface passing through the measurement point and an optical axis of the illuminating part,
    the light receiving optical system is arranged above the measurement point,
    the optical unit further includes a second reflecting mirror that modifies the traveling directions of the measurement light beams from the plurality of reflecting mirrors toward the light receiving optical system, and
    in a case where the second reflecting mirror is not provided, the light receiving optical system is arranged at an arrangement position where the optical axis of the light receiving optical system coincides with a virtual perpendicular line passing through the measurement point and orthogonal to the reference plane.

12. The optical unit for a multi-angle optical characteristic measuring device according to claim 2, further comprising
a branching part that causes part of the illuminating light beam to branch off as a branch light beam, the branching part being arranged between the illuminating part and the measurement point such that the branch light beam is detected by the two-dimensional detecting part, wherein
a hardware processor obtains optical characteristics further based on a second result of detection of the branch light beam detected by the two-dimensional detecting part.

13. A multi-angle optical characteristic measuring device comprising:
the optical unit for a multi-angle optical characteristic measuring device according to claim 2; and
a hardware processor that obtains predetermined optical characteristics of a subject facing the measurement point based on results of detection of the measurement light beams detected by the two-dimensional detecting part.

14. The optical unit for a multi-angle optical characteristic measuring device according to claim 3, wherein
each of the plurality of reflecting mirrors is arranged on a virtual reference plane including a normal of the measurement surface passing through the measurement point and an optical axis of the illuminating part,
the light receiving optical system is arranged above the measurement point,
the optical unit further includes a second reflecting mirror that modifies the traveling directions of the measurement light beams from the plurality of reflecting mirrors toward the light receiving optical system, and
in a case where the second reflecting mirror is not provided, the light receiving optical system is arranged at an arrangement position where the optical axis of the light receiving optical system coincides with a virtual perpendicular line passing through the measurement point and orthogonal to the reference plane.

15. The optical unit for a multi-angle optical characteristic measuring device according to claim 3, further comprising
a branching part that causes part of the illuminating light beam to branch off as a branch light beam, the branching part being arranged between the illuminating part and the measurement point such that the branch light beam is detected by the two-dimensional detecting part, wherein
a hardware processor obtains optical characteristics further based on a second result of detection of the branch light beam detected by the two-dimensional detecting part.

16. A multi-angle optical characteristic measuring device comprising:
the optical unit for a multi-angle optical characteristic measuring device according to claim 3; and
a hardware processor that obtains predetermined optical characteristics of a subject facing the measurement point based on results of detection of the measurement light beams detected by the two-dimensional detecting part.

17. The optical unit for a multi-angle optical characteristic measuring device according to claim 4, wherein
each of the plurality of reflecting mirrors is arranged on a virtual reference plane including a normal of the measurement surface passing through the measurement point and an optical axis of the illuminating part,
the light receiving optical system is arranged above the measurement point,
the optical unit further includes a second reflecting mirror that modifies the traveling directions of the measurement light beams from the plurality of reflecting mirrors toward the light receiving optical system, and
in a case where the second reflecting mirror is not provided, the light receiving optical system is arranged at an arrangement position where the optical axis of the light receiving optical system coincides with a virtual perpendicular line passing through the measurement point and orthogonal to the reference plane.

18. The optical unit for a multi-angle optical characteristic measuring device according to claim 4, further comprising
a branching part that causes part of the illuminating light beam to branch off as a branch light beam, the branching part being arranged between the illuminating part and the measurement point such that the branch light beam is detected by the two-dimensional detecting part, wherein
a hardware processor obtains optical characteristics further based on a second result of detection of the branch light beam detected by the two-dimensional detecting part.

19. A multi-angle optical characteristic measuring device comprising:
the optical unit for a multi-angle optical characteristic measuring device according to claim 4; and
a hardware processor that obtains predetermined optical characteristics of a subject facing the measurement point based on results of detection of the measurement light beams detected by the two-dimensional detecting part.

20. The optical unit for a multi-angle optical characteristic measuring device according to claim 5, wherein
each of the plurality of reflecting mirrors is arranged on a virtual reference plane including a normal of the measurement surface passing through the measurement point and an optical axis of the illuminating part,
the light receiving optical system is arranged above the measurement point,
the optical unit further includes a second reflecting mirror that modifies the traveling directions of the measurement light beams from the plurality of reflecting mirrors toward the light receiving optical system, and
in a case where the second reflecting mirror is not provided, the light receiving optical system is arranged at an arrangement position where the optical axis of the light receiving optical system coincides with a virtual perpendicular line passing through the measurement point and orthogonal to the reference plane.

* * * * *